(12) United States Patent
Kim et al.

(10) Patent No.: US 11,578,108 B2
(45) Date of Patent: Feb. 14, 2023

(54) AMPHIPHYSIN-I MUTANT HAVING ANTI-SENESCENCE ACTIVITY AND USE THEREOF

(71) Applicant: Chungbuk National University Industry-Academic Cooperation Foundation, Chungcheongbuk-do (KR)

(72) Inventors: Eung Gook Kim, Chungcheongbuk-do (KR); Eun Young Shin, Chungcheongbuk-do (KR)

(73) Assignee: Chungbuk National University Industrial-Academic Cooperation Foundation, Chungcheongbuk-do (KR)

( * ) Notice: Subject to any disclaimer, the term of this patent is extended or adjusted under 35 U.S.C. 154(b) by 0 days.

(21) Appl. No.: 17/211,808

(22) Filed: Mar. 24, 2021

(65) Prior Publication Data

US 2022/0306709 A1    Sep. 29, 2022

(51) Int. Cl.
   *A61K 38/17*  (2006.01)
   *A61K 38/00*  (2006.01)
   *C07K 14/47*  (2006.01)

(52) U.S. Cl.
   CPC .......... *C07K 14/4703* (2013.01); *A61K 38/00* (2013.01)

(58) Field of Classification Search
   CPC .... A61K 38/00; A61K 38/17; C07K 14/4703; C07K 14/47
   See application file for complete search history.

(56) References Cited

U.S. PATENT DOCUMENTS 6,753,314 B1 * 6/2004 Giot .................... C07K 14/395 435/7.1

FOREIGN PATENT DOCUMENTS

| KR | 1020020020295 A | 2/2004 |
|---|---|---|
| KR | 100460190 | 12/2004 |

OTHER PUBLICATIONS

NCBI, "Amphiphysin [*Homo sapiens*]," National Center for Biotechnology Information, U.S. National Library of Medicine, https://www.ncbi.nlm.nih.gov/protein/AAH34376.1, last accessed Jun. 25, 2021; 3 pages.

Wu, Yumei, et al. "Truncations of amphiphysin I by calpain inhibit vesicle endocytosis during neural hyperexcitation," The EMBO Journal; vol. 26, No. 12, European Molecular Biology Organization, May 31, 2007, pp. 2981-2990.

Wu, Yumei, et al., "Amphiphysin I and regulation of synaptic vesicle endocytosis," Acta Medica Okayama, vol. 63, Issue 6, Article 2, Dec. 2009, Okayama University Medical School, 21 pages.

* cited by examiner

*Primary Examiner* — Julie Ha
(74) *Attorney, Agent, or Firm* — Culhane Meadows PLLC; Robert Klinger

(57) ABSTRACT

Disclosed are an amphiphysin-I mutant having anti-senescence activity and the use thereof. More particularly, disclosed are an amphiphysin-I mutant (AMPH-I) wherein valine (V), which is the 392nd amino acid in the amino acid sequence of amphiphysin-I (AMPH-I) represented by SEQ ID NO: 1, is substituted with glycine (G), a composition for suppressing aging and cellular senescence containing the amphiphysin-I mutant as an active ingredient, a pharmaceutical composition for preventing or treating senescence or a senescence-associated disease, a method for suppressing aging and cellular senescence, and a method for screening an inhibitor for aging and cellular senescence. The amphiphysin-I mutant is capable of suppressing both promotion of aging and cellular senescence and reduction of endocytosis caused by suppression of expression of βPIX (PAK1-interacting exchange factor beta), of preventing cleavage of the amphiphysin-I protein caused by calpain, a protease involved in aging and cellular senescence caused by suppressed βPIX expression, and of suppressing the expression of aging and cellular senescence indicators. Thus, the amphiphysin-I mutant is effectively used as a novel therapeutic agent for senescence or senescence-associated diseases.

5 Claims, 33 Drawing Sheets

Specification includes a Sequence Listing.

AMPHIPHYSIN-I MUTANT HAVING ANTI-SENESCENCE ACTIVITY AND USE THEREOF

BACKGROUND OF THE INVENTION

Field of the Invention

The present invention relates to an amphiphysin-I mutant having anti-senescence activity and the use thereof.

Description of the Related Art

Cellular senescence (cellular aging) is a major cause of aging in subjects, and is due to a number of factors such as DNA damage, telomere erosion, accumulation of cellular stress, and loss of cell replication ability. Indicators of determining cellular senescence are known to include morphological features in which aged cells become large and flat in shape, heterochromatin increases in the nucleus and the number of vacuoles increases in the cytoplasm, as well as an increase in SA-β-gal (senescence-associated β-galactosidase) activity, increases in the amounts of proteins that suppress cell growth such as p53, p16/INK4 (p16), and p21, and secretion of various inflammatory proteins such as insulin-like growth factor binding proteins (IGFBPs), interleukin-6, transforming growth factor-β (TGF-β), and interferon.

Such cellular senescence contributes to the aging of subjects or tissue, and greatly affects the pathogenesis of various diseases. Aged cells are often found in inflammatory lesion tissues such as rheumatoid arthritis, osteoarthritis, hepatitis, chronic skin injury and arteriosclerotic vascular tissue and the like, and cellular senescence is also observed in prostate hyperplasia, hepatitis, liver cancer and the like.

Aged cells do not divide well, upon accumulation thereof, so the damaged tissue cannot be properly repaired, and enzymes and inflammatory cytokines that degrade surrounding tissue are secreted, which accelerates tissue damage and thus cause senescence-associated diseases. Thus, cellular senescence may be considered to be a fundamental cause of aging, and thus research with the goal of delaying cellular senescence, in particular, research to find substances that can regulate cellular senescence and use the same for the prevention and treatment of diseases, is underway.

It is known that cellular senescence remarkably deteriorates the responsiveness of cells to external stimuli and reduces the function of cell membrane receptor endocytosis. In this regard, the result of analysis of cell membrane receptor-mediated transferrin endocytosis in young cells and aged cells showed that endocytosis of transferrin mediated by cell membrane receptors in aged cells is remarkably reduced compared to young cells.

In addition, it is known that cell membrane receptor-mediated endocytosis occurs through several steps via clathrin-coated vesicles, and clathrin, AP2, dynamin, amphiphysin-I and the like are involved in this process.

Meanwhile, amphiphysin proteins contribute to the creation of clathrin-mediated endocytosis (CME) endocytic pits by generating curvature in the cell membrane, and dynamin proteins are G proteins having GTPase activity and create endocytic vesicles by cleaving the neck of old endocytic pits. Such endocytosis is also involved in the dissolution of focal adhesion (FA) induced by integrin, and thus plays a key role in various cellular functions regulated by cell adhesion, that is, cell growth, differentiation, and death.

In addition, it has been reported that, in aged cells, the expression of amphiphysin-I protein is reduced and that endocytosis by receptors is thus regulated. For this reason, the amphiphysin-I protein is predicted to be useful for regulating aging. However, there is almost no research on the specific mechanism of action forming the basis for the relationship between the amphiphysin-I protein and senescence.

PRIOR ART (Patent Document 1) Korean Patent No. 10-0460190

SUMMARY OF THE INVENTION

Accordingly, the present inventors found that cellular senescence was promoted and that endocytosis was reduced by suppression of the expression of βPIX (PAK1-interacting exchange factor beta). During this process, the present inventors found that the amphiphysin-I (AMPH-I) protein was caused by cleavage by calpain, a protease. In this regard, the result of treatment of aging cells with an amphiphysin-I mutant (AMPH-V329G), which impedes calpain-mediated cleavage, showed that the expression of cellular senescence indicators was inhibited and endocytosis reduced by aging, was recovered again. This means that the amphiphysin-I mutant of the present invention is useful as an inhibitor for cellular senescence. Based on this finding, the present invention has been completed.

Accordingly, it is one object of the present invention to provide an amphiphysin-I mutant (AMPH-I) wherein valine (V), which is the 392nd amino acid in the amino acid sequence of amphiphysin-I (AMPH-I) represented by SEQ ID NO: 1, is substituted with glycine (G).

Accordingly, it is another object of the present invention to provide a composition for suppressing cellular senescence containing the amphiphysin-I mutant of the present invention as an active ingredient.

It is another object of the present invention to provide a pharmaceutical composition for preventing or treating senescence or a senescence-associated disease, containing the amphiphysin-I mutant of the present invention as an active ingredient.

It is another object of the present invention to provide a method for suppressing cellular senescence including treating isolated cells with an expression vector containing the amphiphysin-I mutant of the present invention or a gene encoding the same.

It is another object of the present invention to provide a method for screening an inhibitor for cellular senescence including treating cells expressing the amphiphysin-I protein having an amino acid sequence of SEQ ID NO: 1 with a candidate substance, and detecting whether or not the 392nd amino acid in the amphiphysin-I protein of SEQ ID NO: 1 is cleaved by the candidate substance.

In accordance with the present invention, the above and other objects can be accomplished by the provision of an amphiphysin-I mutant (AMPH-I) wherein valine (V), which is the 392nd amino acid in the amino acid sequence of amphiphysin-I (AMPH-I) represented by SEQ ID NO: 1, is substituted with glycine (G).

In accordance with another aspect of the present invention, provided is a composition for suppressing cellular senescence containing the amphiphysin-I mutant of the present invention as an active ingredient.

In an embodiment of the present invention, the amphiphysin-I mutant may suppress cellular senescence caused by suppression of expression of βPIX (PAK1-interacting exchange factor beta), and may suppress the inhibition of endocytosis.

In one embodiment of the present invention, the amphiphysin-I mutant may be characterized in that the 392nd amino acid site in the amino acid sequence of SEQ ID NO: 1 is not cleaved by calpain, a protease.

In accordance with another aspect of the present invention, provided is a pharmaceutical composition for preventing or treating senescence or a senescence-associated disease containing the amphiphysin-I mutant of the present invention as an active ingredient.

In one embodiment of the present invention, the senescence or senescence-associated disease may be a disease caused by suppression of expression of βPIX (PAK1-interacting exchange factor beta).

In one embodiment of the present invention, the amphiphysin-I mutant may have activity of suppressing SA-β-galactosidase activity, activity of suppressing expression of a p16 protein, activity of suppressing a decrease of transferrin endocytosis, and activity of suppressing a decrease in integrin β1 endocytosis.

In accordance with another aspect of the present invention, provided is a method for suppressing cellular senescence including treating isolated cells with an expression vector containing the amphiphysin-I mutant of the present invention or a gene encoding the same.

In accordance with another aspect of the present invention, provided is a method for screening an inhibitor for cellular senescence including treating cells expressing the amphiphysin-I protein having an amino acid sequence of SEQ ID NO: 1 with a candidate substance, and detecting whether or not the 392nd amino acid of the amphiphysin-I protein represented by SEQ ID NO: 1 is cleaved by the candidate substance.

In one embodiment of the present invention, the cellular senescence may be caused by suppression of expression of βPIX (PAK1-interacting exchange factor beta).

In an embodiment of the present invention, the method may further include determining the candidate substance to be an inhibitor for cellular senescence when the candidate substance does not cleave the 392nd amino acid of the amphiphysin-I protein represented by SEQ ID NO: 1.

BRIEF DESCRIPTION OF THE DRAWINGS

The above and other objects, features and other advantages of the present invention will be more clearly understood from the following detailed description taken in conjunction with the accompanying drawings, in which:

FIG. 1H is a microscope image showing the SA-β-Gal positive cells detected through SA-β-Gal staining;

DETAILED DESCRIPTION OF ILLUSTRATIVE EMBODIMENTS

In the present invention it is identified for the first time that a mutant (V392G) of the amphiphysin-I (AMPH-I) protein has activity of suppressing aging (senescence).

During research on a novel aging regulation mechanism, the present inventors found that the expression of βPIX (PAK1-interacting exchange factor beta) was reduced in aged cells. In addition, it was found that the endocytosis of activated integrin β1 and transferrin was reduced in aged cells exhibiting reduced expression of βPIX compared to young cells and that this is caused by the phenomenon in which the amphiphysin-I protein that regulates endocytosis is cleaved by calpain, which is a protease.

Figure 1A:
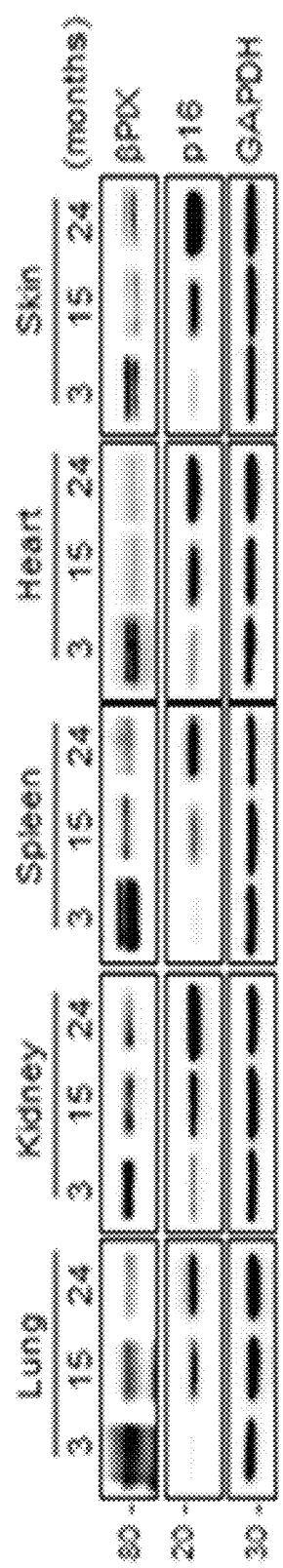
FIG. 1A shows the result of immunoblotting for detecting the expression level of βPIX in tissues (lung, kidney, spleen, heart, and skin) obtained from mice aged 3, 15, and 24 months.
Figure 1B:
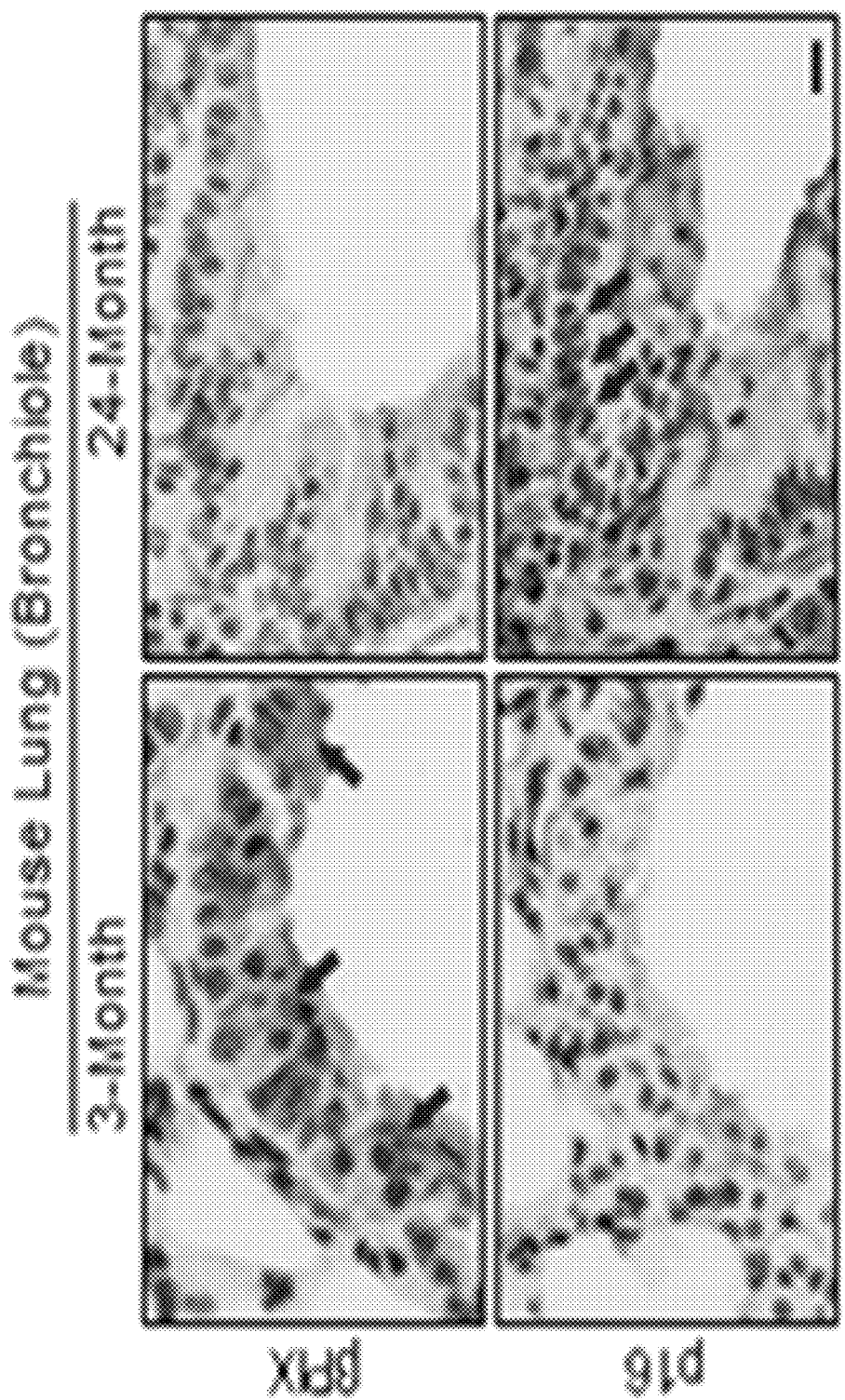
FIG. 1B shows the result of immunohistochemistry for detecting the expression levels of βPIX and p16 in lung tissue of each mouse.
Figure 1C:
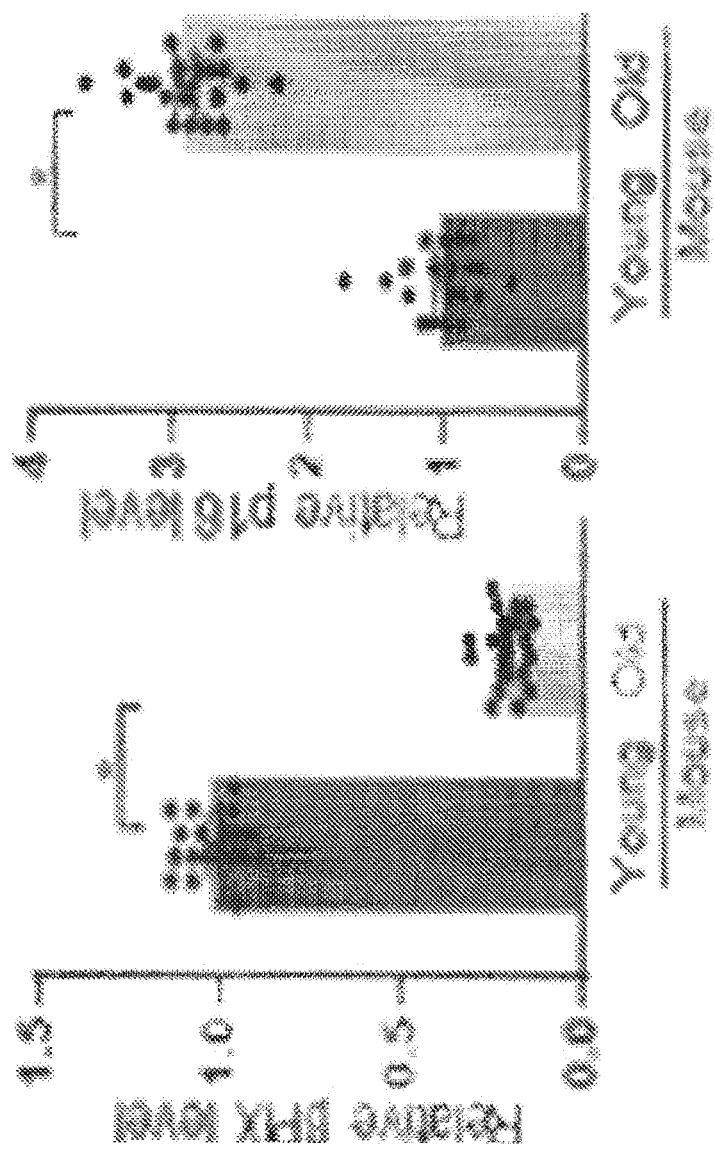
FIG. 1C is a bar graph showing the expression levels of βPIX and p16 obtained by immunohistochemistry.
Figure 1D:
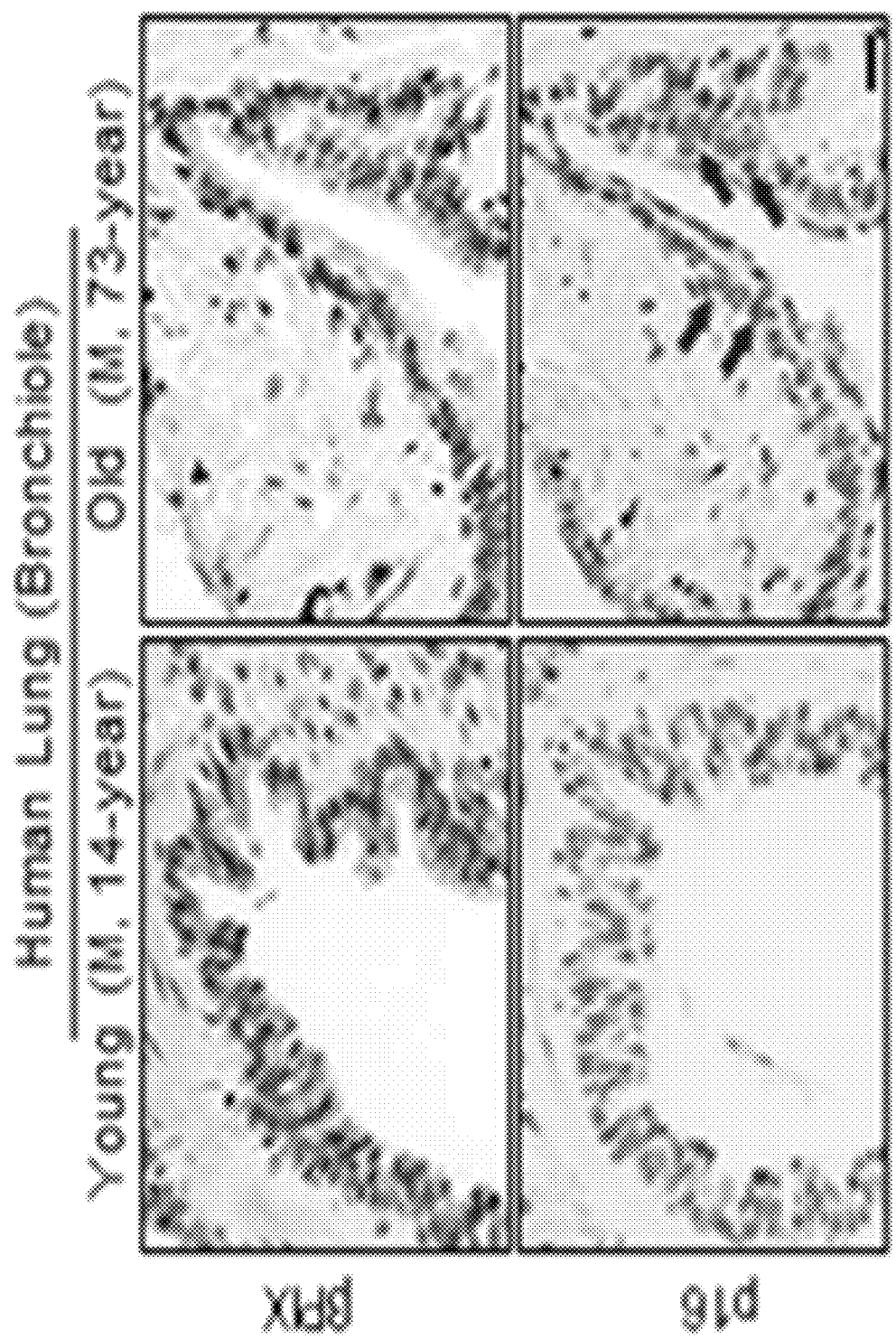
FIG. 1D shows the results of immunohistochemistry for detecting the expression levels of βPIX and p16 in lung tissue obtained from young and old subjects and the expression levels thereof.
Figure 1E:
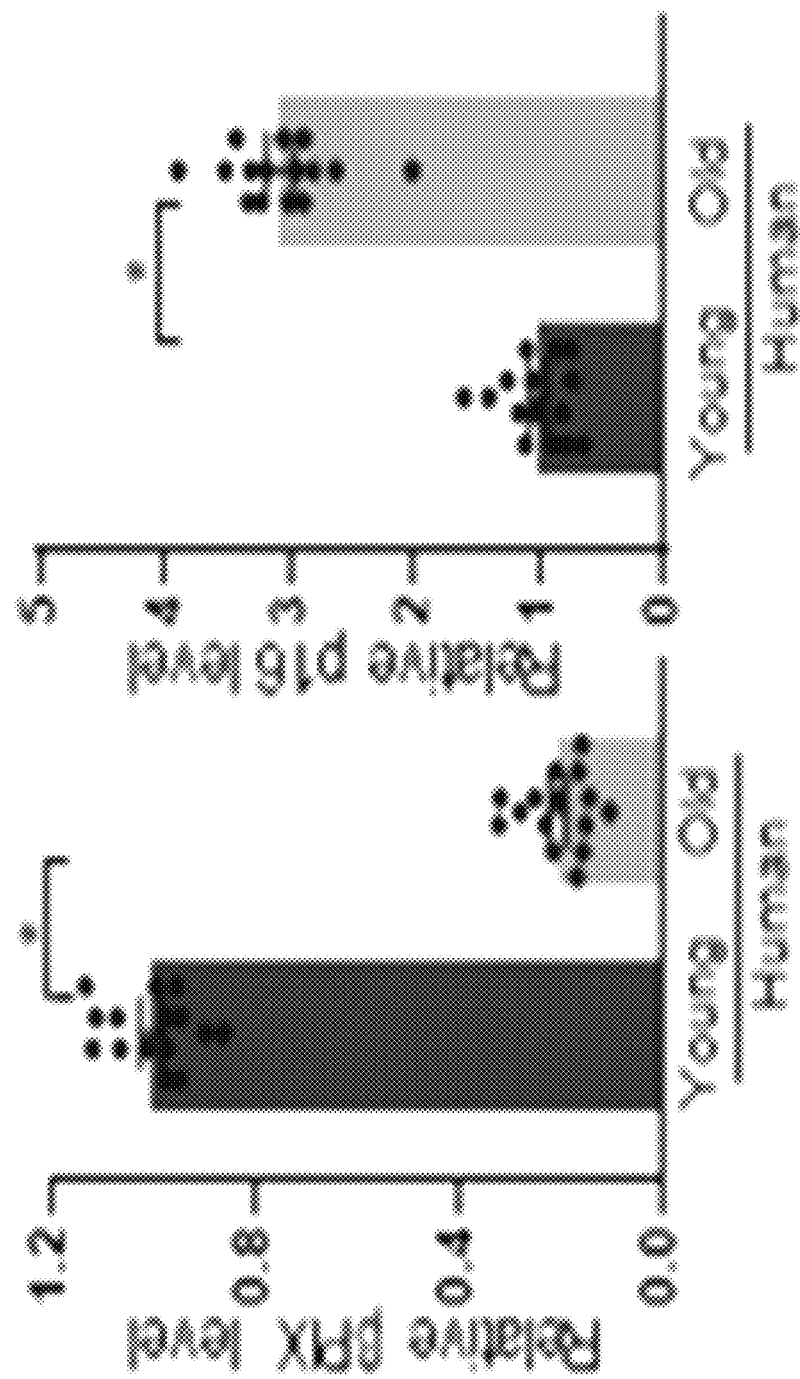
FIG. 1E is a bar graph showing the results of immunohistochemistry for detecting the expression levels of βPIX and p16 in lung tissue obtained from young and old subjects and the expression levels thereof.
Figure 1F:
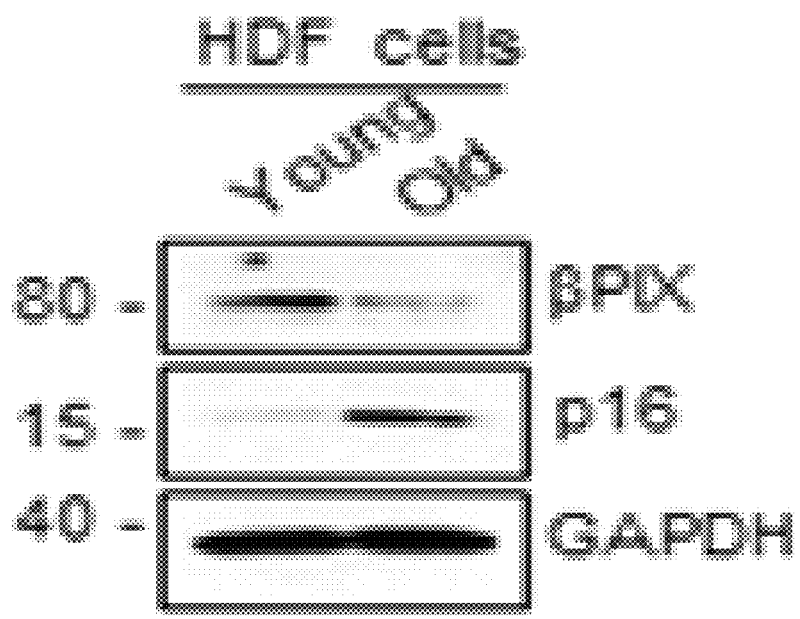
FIG. 1F shows the result of immunoblotting for detecting the expression levels of βPIX and p16 in HDF cells subjected to different passage culture methods.
Figure 1G:
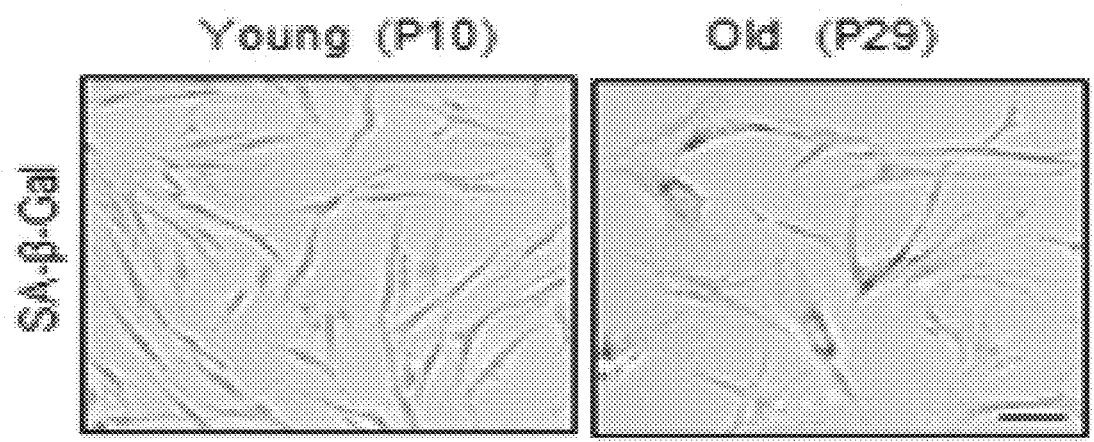
FIG. 1G is a microscope image showing the SA-β-Gal positive cells detected through SA-β-Gal staining.
Figure 1H:
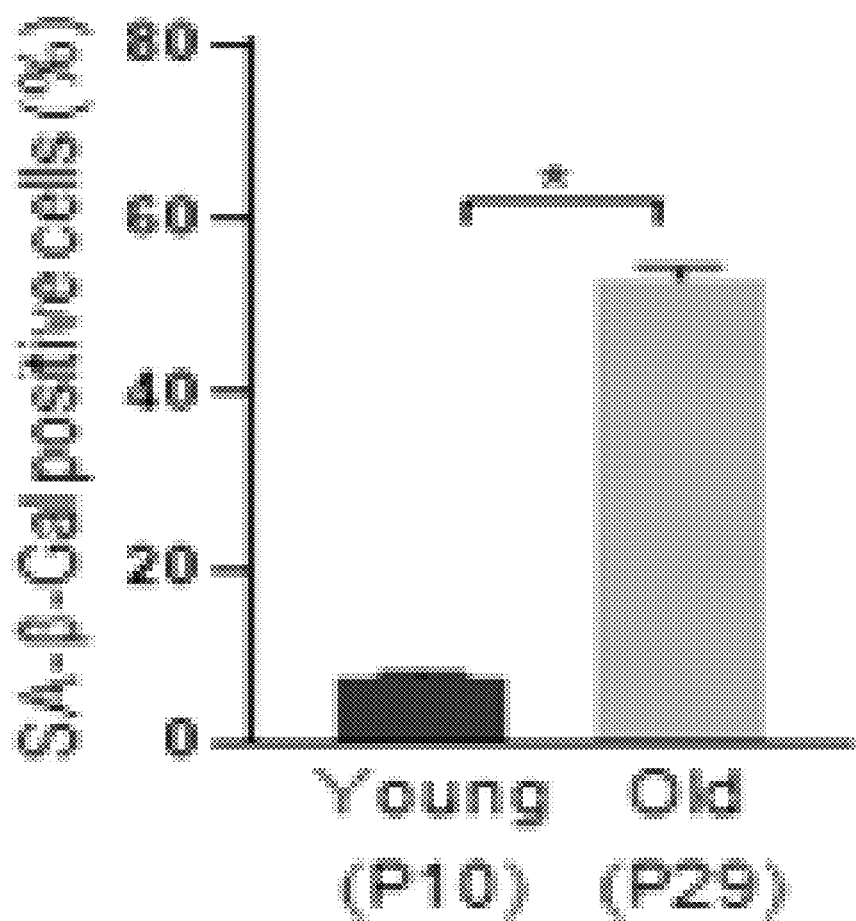
FIG. 1H shows the result of SA-β-Gal activity assay analysis.
Figure 2A:
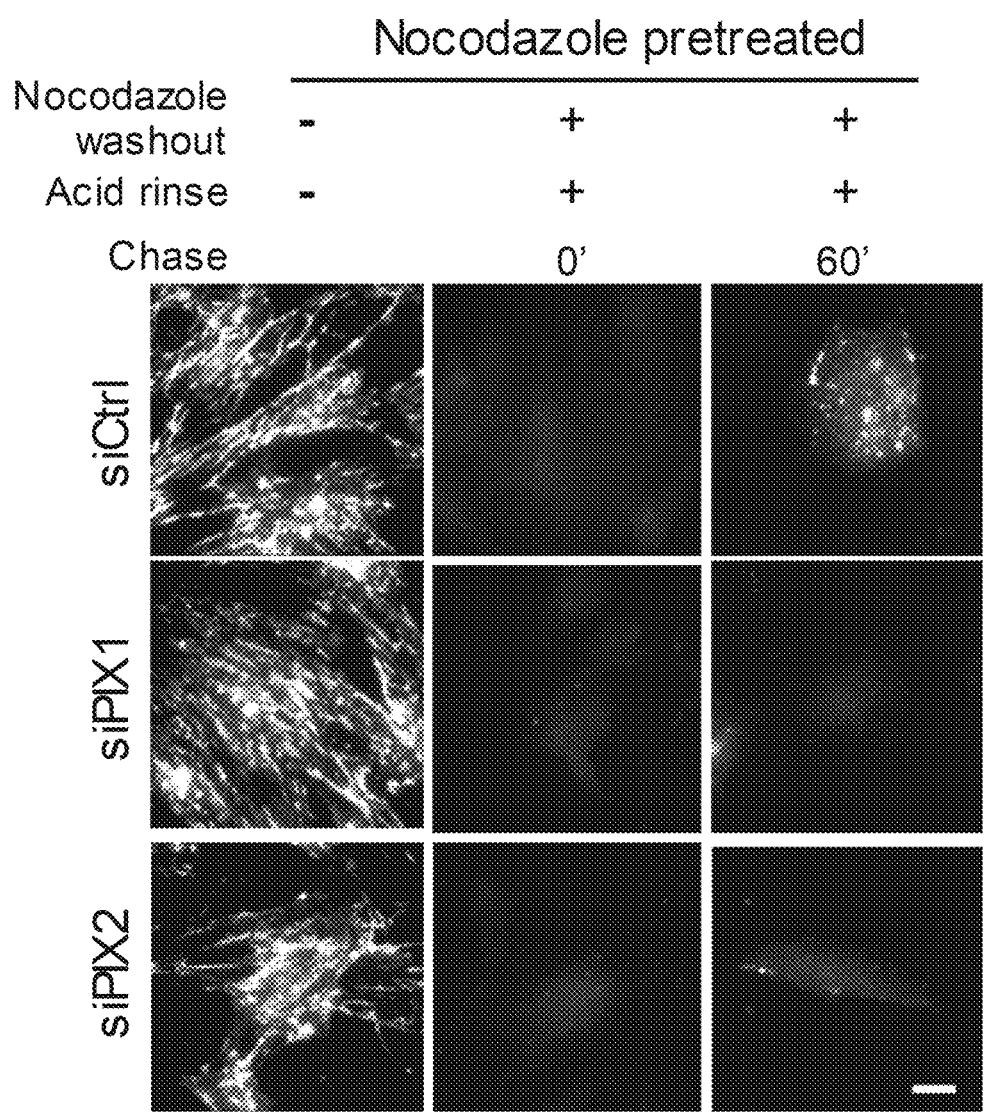
FIG. 2A is an image showing endocytosis of integrin β1 detected using staining an active integrin β1 antibody after treatment of HDF cells treated with siRNA for βPIX with nocodazole.
Figure 2B:
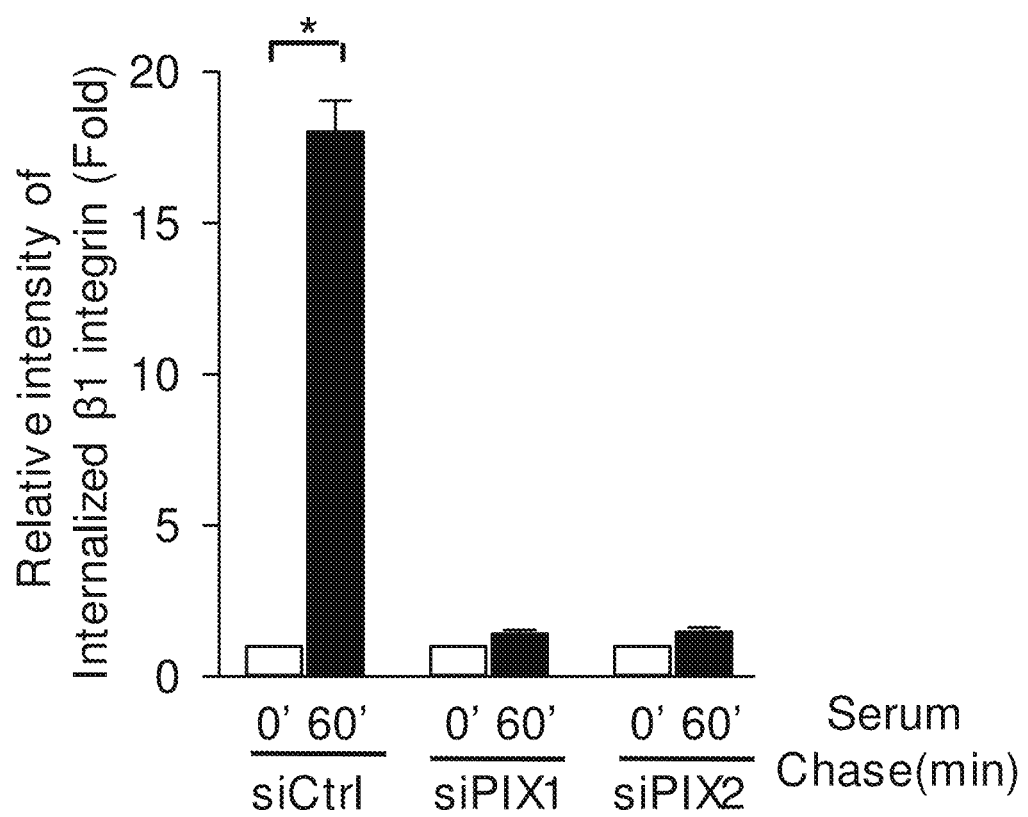
FIG. 2B shows the result of quantitative measurement showing the degree of endocytosis of integrin β1.
Figure 2C:
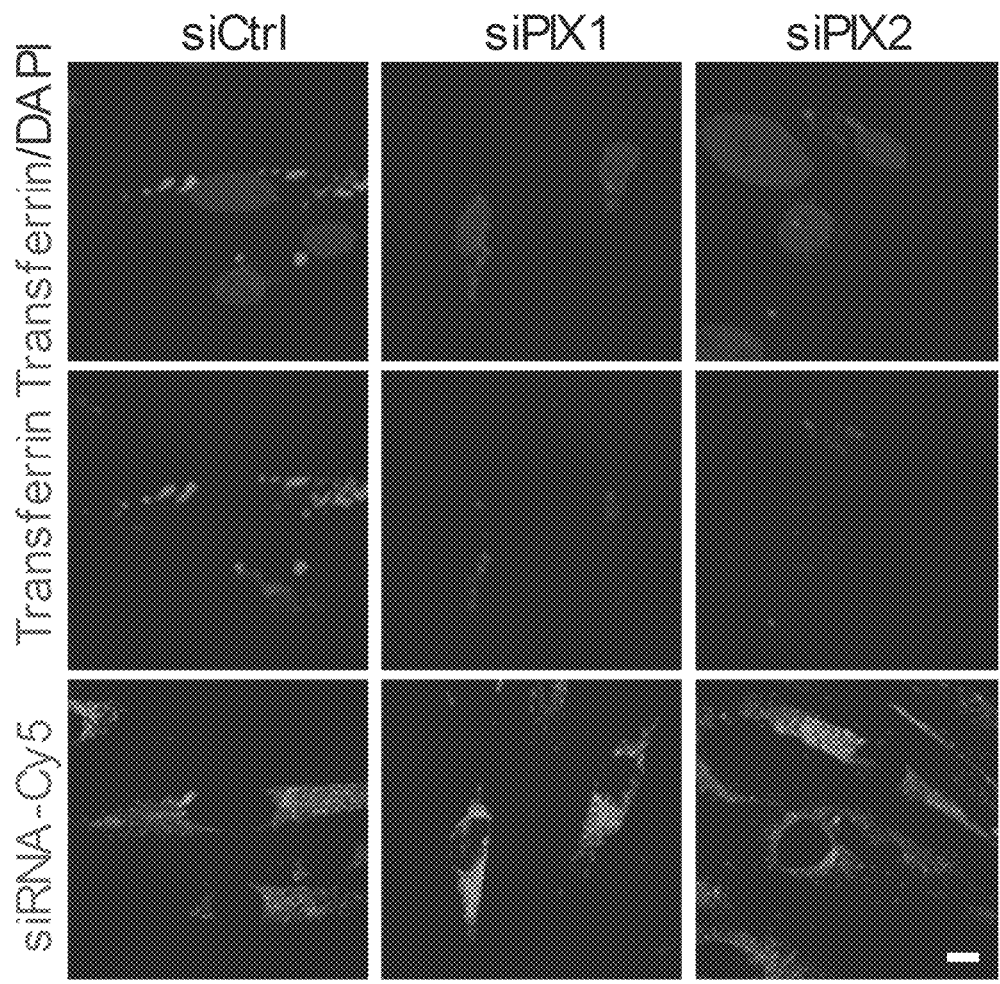
FIG. 2C is a fluorescence microscope image showing transferrin endocytosis from HDF cells treated with siRNA for βPIX.
Figure 2D:
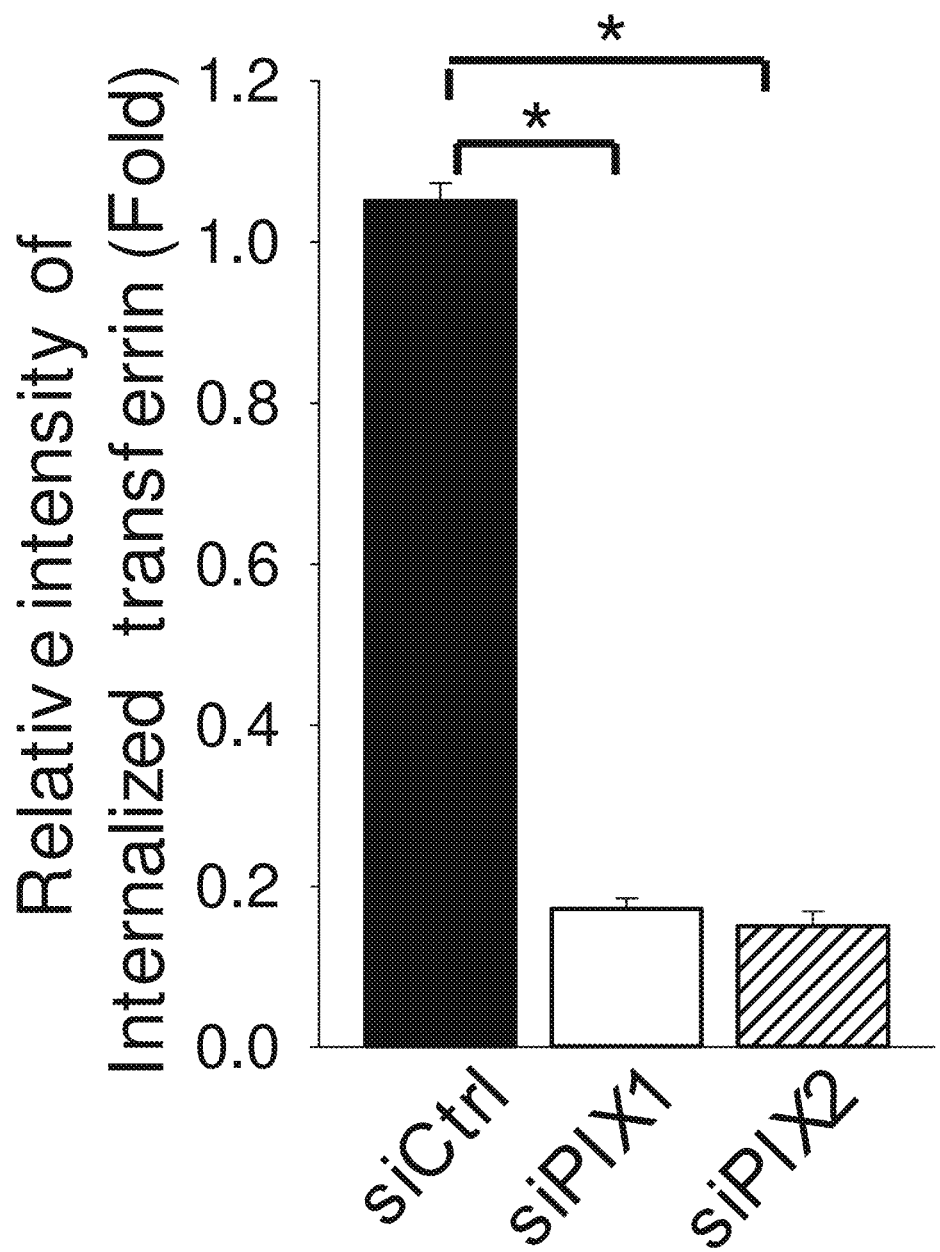
FIG. 2D shows the result of quantitative measurement showing the degree of transferrin endocytosis.
Figure 2E:
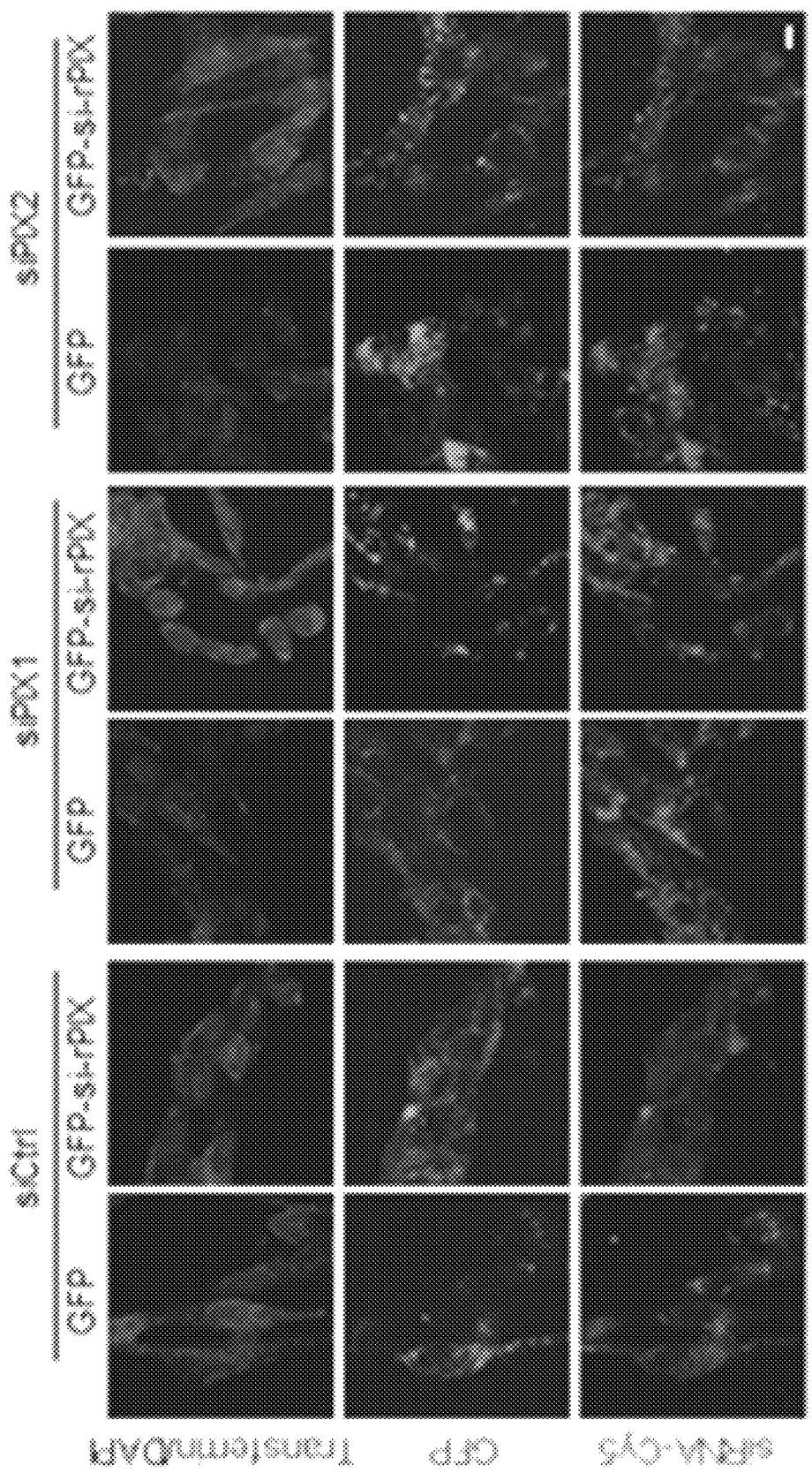
FIG. 2E shows the result of confocal microscopy analysis for detecting the degree of transferrin endocytosis in lung tissue of mice injected with siRNA for βPIX.
Figure 2F:
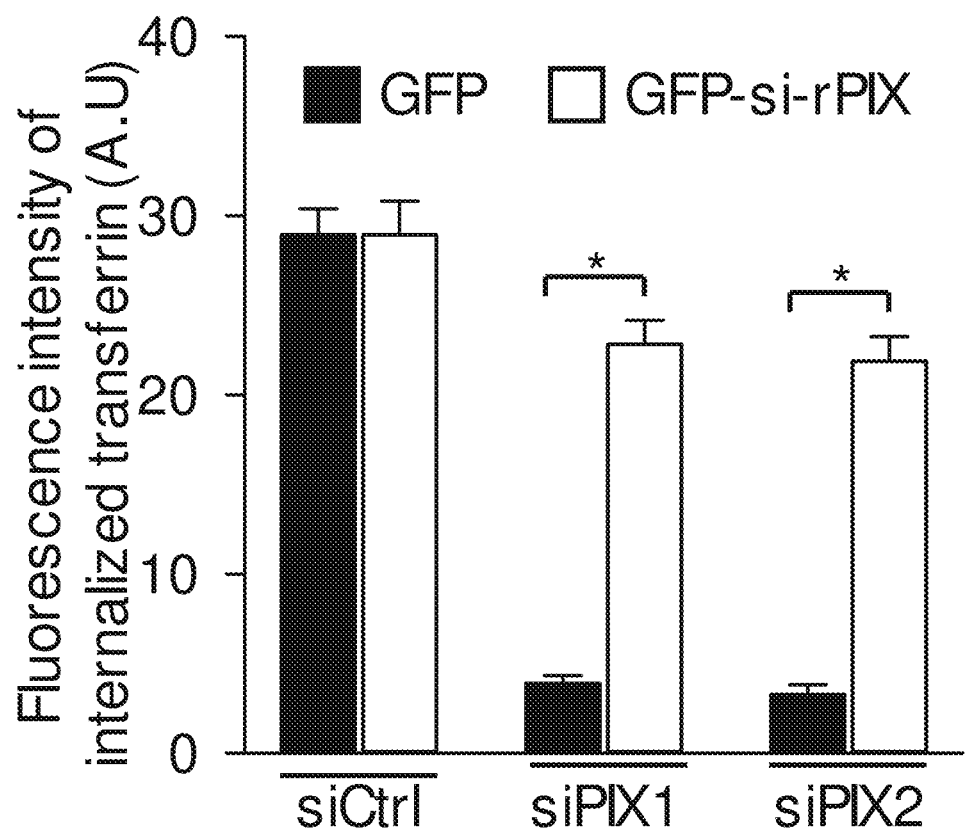
FIG. 2F is a bar graph showing the result of quantitative measurement thereof.
Figure 2G:
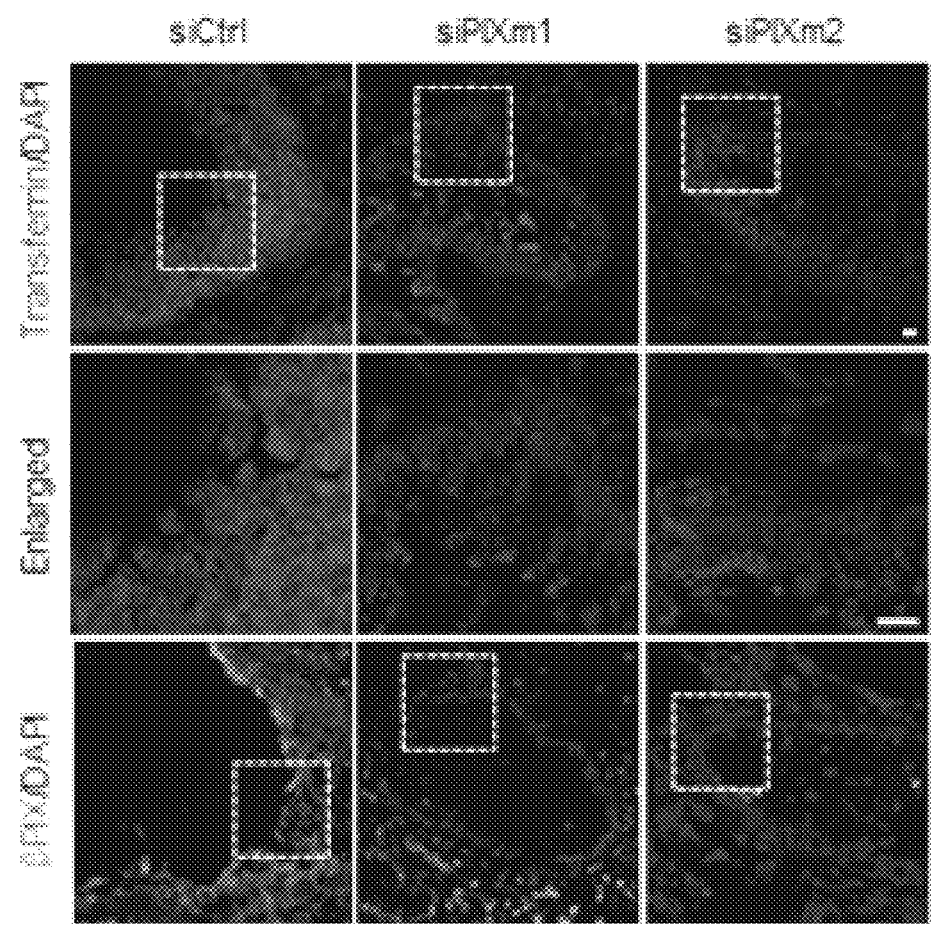
FIG. 2G shows transferrin endocytosis in the bronchi of siRNA-treated mice, (Transferrin was applied by the intratracheal delivery technique. Internalized transferrin was observed with confocal microscope. Scale bars, 10 μm.)
Figure 2H:
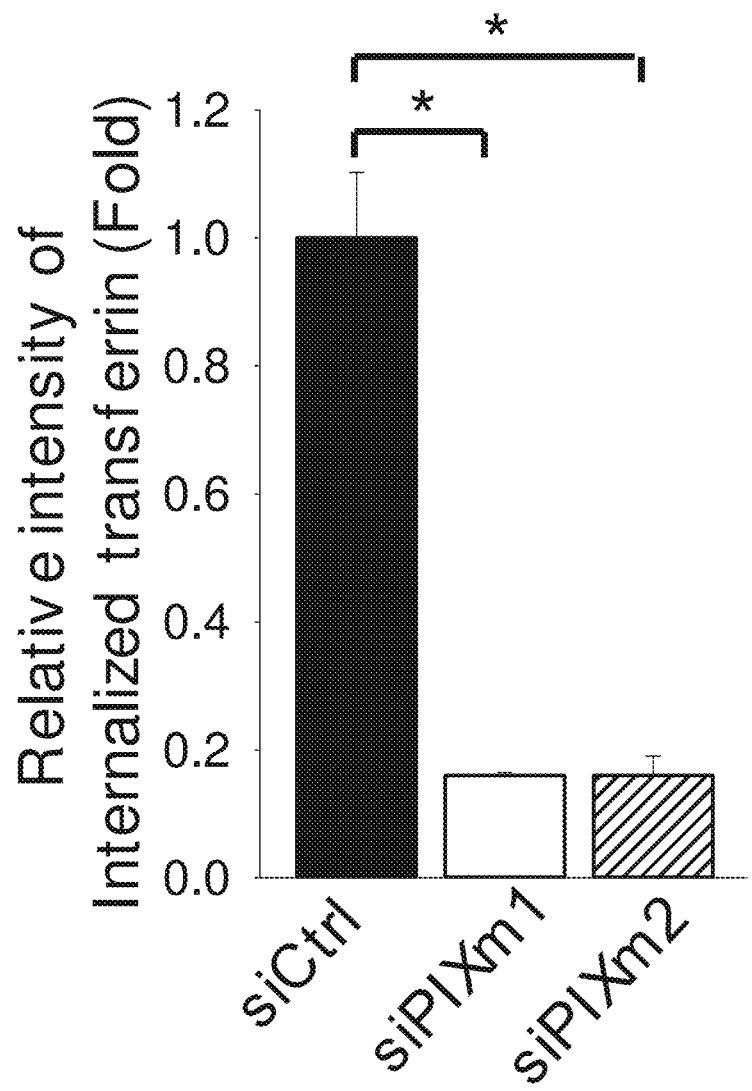
FIG. 2H is a bar graph showing the result of quantitative measurement showing the degree of internalized transferrin.

According to an embodiment of the present invention, a change in the expression level of βPIX depending on aging was first analyzed. The result of measurement of expression levels of βPIX proteins in tissues such as lung, kidney and skin tissues obtained from 1-month-old young mice and 24-month-old mice showed that all tissues obtained from old mice exhibited a remarkably reduced expression level of βPIX compared to tissues obtained from young mice (see FIG. 1A). This result was the same as in human fibroblasts (HDF). In addition, the decreased expression of βPIX and increased expression of p16, which are indicators of senescence, were found in lung tissues of young and old mice and humans (FIGS. 1B to 1E). Aged HDF cells exhibited remarkably reduced expression of βPIX compared to young HDF cells, and also exhibited increased expression of p16 and increased activity of SA-β-gal (senescence-associated β-galactosidase), which are known other senescence indicators (FIGS. 1F to 1H). This proved that βPIX is closely associated with senescence and that inhibition of the expression or activity of βPIX can be a major cause of senescence.

In addition, in another embodiment of the present invention, the relationship between cellular senescence and endocytosis was analyzed and the result showed that endocytosis of integrin β1 and transferrin was reduced in aged cells (see FIG. 2).

In addition, the amphiphysin-I protein, known to be involved in endocytosis, was cleaved in cells aged due to suppression of βPIX expression, and thus a protein fragment of about 50 kDa was identified. This cleavage phenomenon does not occur in cells in which expression of βPIX is not suppressed, in other words, in non-aged cells, and experiments performed on lung tissues of young mice and old mice showed the same results as above (see FIG. 3).

In addition, cleavage of endocytosis regulatory proteins in aged cells or tissues has been found to occur specifically for the amphiphysin-I protein. This can be seen from the fact that dynamin proteins known as endocytosis regulatory proteins do not undergo cleavage induced by cellular senescence (see FIGS. 3A and 3D). This result proved that cleavage of the amphiphysin-I protein, specifically cleavage of the C-terminus thereof, is closely associated with cellular senescence.

Figure 3A:
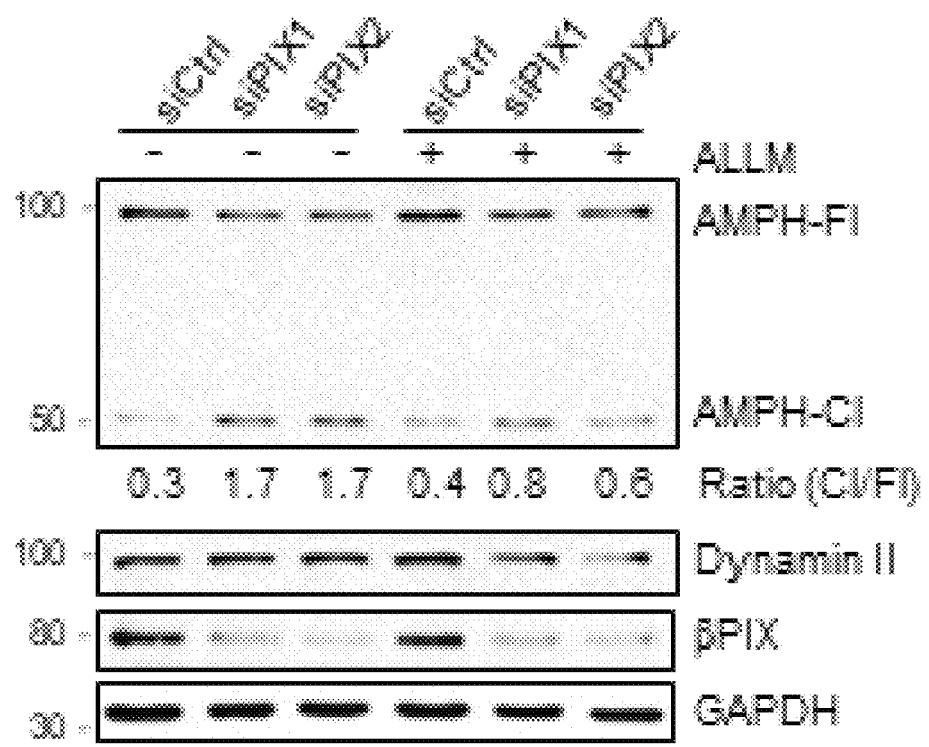
FIG. 3A shows the immunoblotting result detecting the presence or absence of the cleaved fragment after treating HDF cells with βPIX siRNA to induce cellular senescence through βPIX inhibition (AMPH-Fl: full length AMPH-I, AMPH-Cl: cleaved AMPH-I)

Meanwhile, calpain is a calcium-dependent cysteine protease which is known to be capable of cleaving the amphiphysin-I protein. Accordingly, the present inventors identified a phenomenon in which the C-terminus of the amphiphysin-I protein is cleaved in aged cells, and endeavored to determine whether or not this cleavage was caused by calpain. As a result, the C-terminal fragment of the amphiphysin-I protein was not detected in the group of aged cells, in which the expression of βPIX was suppressed, which is treated with a calpain inhibitor, ALLM, compared to the group not treated with ALLM (FIG. 3A). This proved that the C-terminal cleavage of the amphiphysin-I protein depends on calpain in cellular senescence caused by suppressed βPIX expression.

Figure 4A:
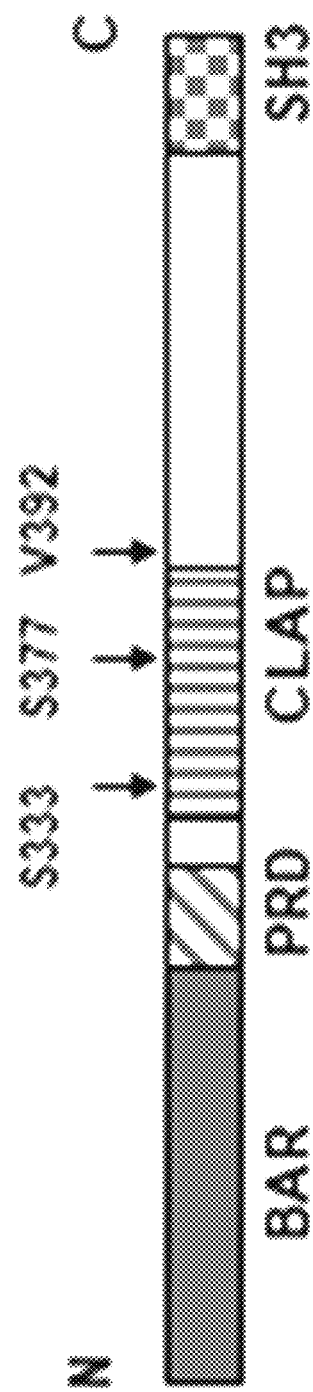
FIG. 4A is a schematic diagram showing the sites (S333, S377, V392) in the AMPH-I protein expected to be cleavable by calpain, in which, in detail.
Figure 4B:
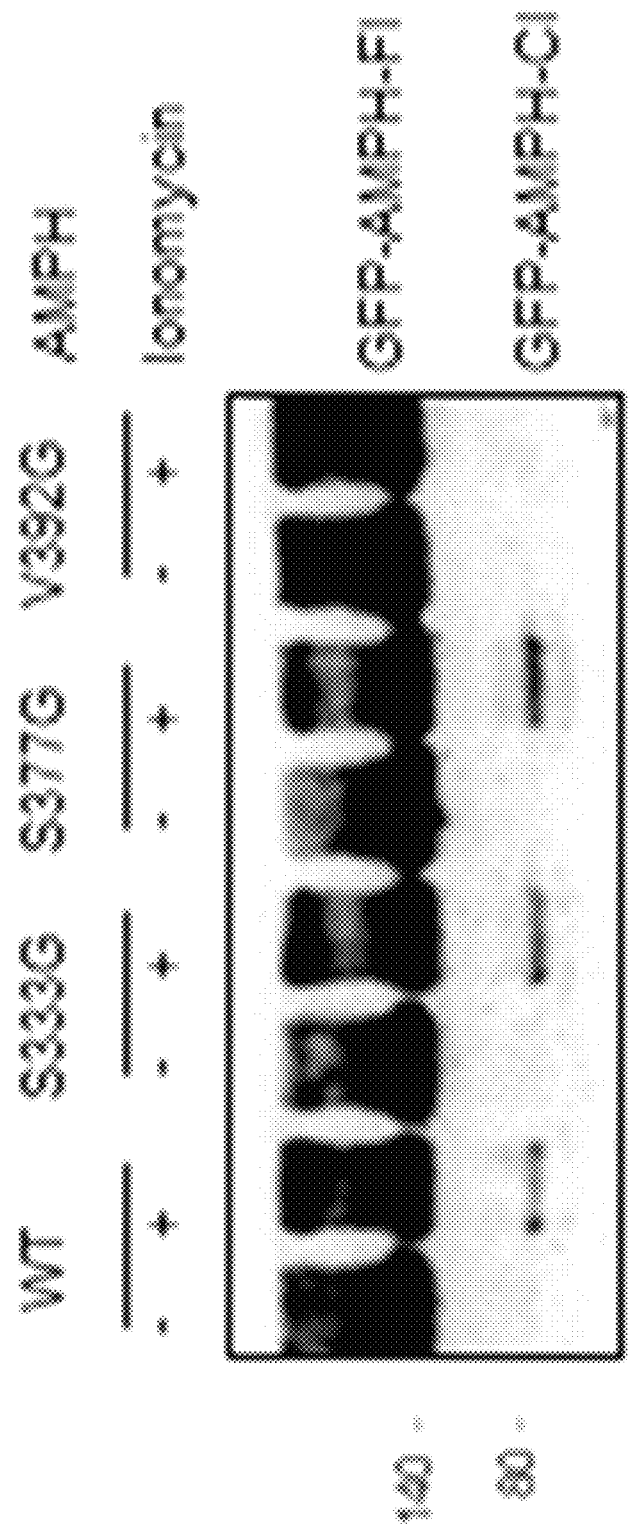
FIG. 4B shows the result of detection as to whether or not mutants S333G, S377G and V392G, obtained by mutating the S333, S377 and V392 sites of AMPH-I, were cleaved by calpain, wherein 293T cell lysates were obtained after transduction into 293T cells with a plasmid containing the polynucleotide of each mutant and immunoblotting was conducted using an antibody of AMPH-I.

Furthermore, in order to identify the site of the amphiphysin-I protein that is cleaved by calpain, the present inventors selected three predicted sites (S333, S377, V392), established mutants (AMPH-S333G, AMPH-S377G, AMPH-V392G) by substituting each of the amino acid sites with glycine (G), and determined whether or not cleavage of each mutant occurred in aged cells (FIG. 4A). The AMPH-S333G and AMPH-S377G mutants were treated with ionomycin, which induces the activation of calpain in aged cells exhibiting suppressed βPIX expression. As a result, C-terminal fragments cleaved by calpain were identified, whereas the cleaved C-terminal fragment could not be observed in the AMPH-V392G mutant (FIG. 4B). This result means that cleavage of the C-terminus of AMPH by calpain in cellular senescence occurs specifically only at the V392 site of AMPH.

Therefore, the present inventors found that the AMPH-V392G mutant, specifically an AMPH-V392G mutant in which valine (V), the amino acid at position 392 in the amino acid sequence of SEQ ID NO: 1 of the AMPH-I protein, is substituted with glycine (G), can suppress calpain-mediated AMPH-I cleavage occurring upon cellular senescence and can suppress cellular senescence, and predicted that the AMPH-V392G mutant can be used as a novel senescence inhibitor.

In another embodiment of the present invention, in order to verify this prediction, HDF cells, which are subjected to aging by suppressing the expression of βPIX, were each treated with AMPH-WT and mutant AMPH-V392G, and then endocytosis and cellular senescence were analyzed. The AMPH1-WT-treated group reduced endocytosis of both transferrin and integrin β1 in HDF cells aged due to suppressed βPIX expression, and also increased the number of SA-β-gal positive cells, which is an indicator of cellular senescence. Meanwhile, in the group treated with the AMPH-V392G mutant of the present invention, there was almost no change in endocytosis of transferrin and integrin β1, and the cellular senescence of cells stained with SA-β-gal was reduced (see FIG. 5).

In addition, experiments performed on mouse lung tissue showed the same results as above. Mouse lungs were infected with AMPH-WT and mutant AMPH-V392G lentivirus, and treated with βPIX siRNA to induce aging of the lungs through suppression of βPIX expression, and then transferrin endocytosis and SA-β-gal activity in each lung tissue were analyzed. The result showed that the group expressing the AMPH-V392G mutant, even if βPIX expression was suppressed, reduced endocytosis suppression and remarkably reduced cellular senescence (see FIG. 6) compared to the group expressing AMPH-WT. This indicates that the AMPH-V392G mutant of the present invention can suppress endocytosis reduction induced by cellular senescence and suppress the expression of senescence indicators, thereby ultimately suppressing senescence.

Thus, the present invention provides an amphiphysin-I mutant (AMPH-V392G) in which valine (V), which is the 392nd amino acid in the amino acid sequence of amphiphysin-I (AMPH-I) represented by SEQ ID NO: 1, is substituted with glycine (G), and the amino acid sequence of the AMPH-V392G mutant according to the present invention is represented by SEQ ID NO: 2.

The amphiphysin-I mutant according to the present invention may suppress cellular senescence caused by suppression of the expression of βPIX (PAK1-interacting exchange factor beta), may suppress inhibition of endocytosis, and may be characterized in that the 392nd amino acid site in the amino acid sequence of SEQ ID NO: 1 is not cleaved by calpain, a protease.

Also, the present invention provides a composition for suppressing cellular senescence containing the amphiphysin-I mutant of the present invention as an active ingredient.

Also, the present invention provides a pharmaceutical composition for preventing or treating senescence or a senescence-associated disease containing the amphiphysin-I mutant of the present invention as an active ingredient.

As described above, the amphiphysin-I mutant of the present invention is a mutant in which valine (V), which is the 392nd amino acid in the amino acid sequence of amphiphysin-I (AMPH-I) represented by SEQ ID NO: 1, is substituted with glycine (G), and has activity of suppressing SA-β-galactosidase activity, activity of suppressing expression of a p16 protein, activity of suppressing a decrease of transferrin endocytosis, and activity of suppressing a decrease in integrin (31 endocytosis.

The amphiphysin-I mutant may be included in the composition in the form of a polypeptide in which valine (V), which is the 392nd amino acid in the amino acid sequence of amphiphysin 1 represented by SEQ ID NO: 1, is substituted with glycine (G), or may be included in the composition in the form of an expression vector containing a gene encoding the amphiphysin-I mutant.

In the present invention, the gene encoding the wild type of the amphiphysin-I protein may have a nucleotide sequence of 2085 bp disclosed in Human AMPH I NM_001635.3 (GenBank number) known in the art.

The vector that can be used in the present invention may be any plasmid, phage, cosmid, viral vector, or other medium known in the art, but is not limited thereto. In addition, in the present invention, the polynucleotide encoding the AMPH-V392G mutant may be isolated from nature or artificially synthesized or modified, one or more nucleic acid bases in the nucleotide sequence encoding the AMPH-V392G mutant may be modified by substitution, deletion or insertion, and the protein expressed by such modification should not have a significant change in biological functionality thereof. The modification described above include modifications to heterologous and homologous genes.

The expression vector according to the present invention can be introduced into cells using a method known in the art. For example, the expression vector can be introduced into cells through transient transfection, microinjection, transduction, cell fusion, calcium phosphate precipitation, liposome-mediated transfection, DEAE dextran-mediated transfection, polybrene-mediated transfection, electroporation, gene gun and other known methods for introducing nucleic acids into cells, but is not limited thereto (Wu et al., J. Bio. Chem., 267:963-967, 1992; Wu and Wu, J. Bio. Chem., 263:14621-14624, 1988).

Preferably, the expression vector may be a lentiviral vector containing an AMPH-V392G mutant gene.

The lentiviral vector of the present invention may be a gene encoding the AMPH-V392G mutant, operably linked to a promoter.

The term "operably linked" means that a gene requiring expression and a regulatory sequence thereof are linked to each other to induce gene expression, and the term "promoter" means a DNA sequence capable of regulating transcription of a specific nucleotide sequence into mRNA when linked to the specific sequence. Typically, the promoter is not applied in all cases, but is present in 5' (i.e., upstream) of the desired nucleotide sequence to be transcribed into mRNA, and provides a site to which RNA polymerase and other transcription factors for initiating transcription specifically bind.

The promoter of the present invention may use a constitutive or regulatory promoter, and is preferably a constitutive promoter. The term "constitutive" used in connection with a promoter means that the promoter is capable of instructing the transcription of an operably linked nucleic acid sequence even in the absence of stimulus (e.g., heat shock, chemicals and the like). Meanwhile, the term "regulatory" promoter means a promoter capable of instructing the transcription level of an operably linked nucleic acid sequence in the presence of stimulus (e.g., heat shock, chemicals and the like), unlike the case of absence of stimulus.

In addition, the vector may further contain a gene encoding a fluorescent protein. The fluorescent protein may be used to detect whether or not a desired gene is expressed in a transduced cell or tissue, and any protein capable of emitting fluorescence when expressed in a cell or tissue may be used without limitation, and green fluorescent protein (GFP), modified green fluorescent protein, enhanced green fluorescent protein (EGFP), red fluorescent protein (RFP), enhanced red fluorescent protein (ERFP), blue fluorescent protein (BFP), enhanced blue fluorescent protein (EBFP), yellow fluorescent protein (YFP), enhanced yellow fluorescent protein (EYFP), indigo fluorescent protein (CFP), and enhanced indigo fluorescent protein (ECFP) may be used, and preferably green fluorescent protein (GFP) may be used.

The pharmaceutical composition according to the present invention may contain a pharmaceutically acceptable carrier in addition to the active ingredient, and examples of the carrier include, but are not limited thereto, carriers commonly used in formulations, such as lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, and the like. The pharmaceutical composition of the present invention may further contain, in addition to the ingredients described above, a lubricant, a wetting agent, a sweetening agent, a flavoring agent, an emulsifying agent, a suspending agent, a preservative, and the like. Suitable pharmaceutically acceptable carriers and formulations are described in detail in Remington's Pharmaceutical Sciences (19th ed., 1995).

A suitable dosage of the pharmaceutical composition of the present invention may be formulated in various ways depending on factors such as the formulation method, mode of administration, and age, weight, gender, pathological condition, food, administration time, route of administration, excretion rate and responsiveness of the patient. Meanwhile, the dosage of the pharmaceutical composition of the present invention is preferably 0.0001 to 100 mg/kg (body weight) per day.

The pharmaceutical composition of the present invention may be administered orally or parenterally, and the parenteral administration may be topical application to the skin, intravenous injection, subcutaneous injection, intramuscular injection, intraperitoneal injection, transdermal administration, or the like. The concentration of the active ingredient contained in the composition of the present invention may be determined in consideration of the purpose of treatment, the condition of the patient, the required administration period, or the like, and is not limited to a specific concentration range.

The pharmaceutical composition of the present invention may be prepared in a unit dosage form, or may be prepared by injection into a multi-dose container by formulation using a pharmaceutically acceptable carrier and/or excipient according to a method that can be easily implemented by those skilled in the art. In this case, the formulation may be in the form of a solution, suspension, or emulsion in an oil or aqueous medium, or may be in the form of an extract, powder, granule, tablet or capsule, and may further contain a dispersant or a stabilizer.

The term "treatment" means reversing or ameliorating the disease or disorder to which the treatment is applied, or one or more symptoms of the disease or disorder, or suppressing or preventing the progression thereof, unless otherwise mentioned herein.

In the present invention, the disease may be senescence or a senescence-associated disease, and the disease may be a senescence-associated disease that may be caused by aging induced by suppression of the expression of βPIX (PAK1-interacting exchange factor beta) and the progression of aging.

The senescence-associated disease may include, but is not limited to, atherosclerosis, skin aging, osteoporosis, rheumatoid osteoarthritis, degenerative osteoarthritis, alopecia, wrinkles and hunchback.

Furthermore, the present invention provides a method for suppressing cellular senescence including treating isolated cells with an expression vector containing the amphiphysin-I mutant of the present invention or a gene encoding the same.

The present invention provides a method for screening an inhibitor for cellular senescence including treating cells expressing the amphiphysin-I protein having an amino acid sequence of SEQ ID NO: 1 with a candidate substance, and detecting whether or not the 392nd amino acid of the amphiphysin-I protein represented by SEQ ID NO: 1 is cleaved by the candidate substance.

The method may further include determining the candidate substance to be an inhibitor for cellular senescence when the candidate substance does not cleave the 392nd amino acid of the amphiphysin-I protein represented by SEQ ID NO: 1.

Hereinafter, the present invention will be described in more detail with reference to examples. The examples are provided only for illustration of the present invention and should not be construed as limiting the scope of the present invention.

PREPARATION EXAMPLE 1

Reagent and Experimental Method

The reagents and experimental methods used in the experiments of Examples are as follows.

Reagent Preparation

Invivofectamine, Lipofectamine 2000, DMEM (Dulbecco's Modified Eagle Medium), FBS (fetal bovine serum), OPTI-MEM, Alexa Fluor 594-conjugated transferrin and Alexa Fluor-conjugated secondary antibody were purchased from Thermo Fisher Scientific (Waltham, Mass.) and used.

Calpain inhibitor II (ALLM), SA-β-gal staining solution and other reagents were purchased from Sigma-Aldrich (St. Louis, Mo.) and used.

In addition, the sequences of siRNAs used in the following experiments are as follows.

```
siPIX1:
5'-UCAACUGGUAGUAAGAGCAAAGUUU-3' siPIX2:
5'-UUGAGCUGCAGAUCCUGACGGAAGC-3' siCtrl:
5'-CCUACGCCACCAAUUUCGU-3' hCalpain-2:
5'-GGCAUUAGAAGAAGCAGGUUU-3' siPIXr1:
5-ACUGGUAGUACGAGCCAAGUU-3' siPIXr2:
5-GGAGGAUUAUGAUCCUGAUAG-3' siPIXm1:
5'-CCAACUGGUAGUACGAGCCAAGUUU-3' siPIXm2:
5'-GAGGACCUAGGAGAGUUCAUGGAAA-3' siFAK:
5'-AACCACCUGGGCCAGUAUUAU-3'
```

Preparation of Experimental Animals

The animals used for experimentation were subjected to all experiments according to approved animal protocols and guidelines set by the Institutional Animal Care and Use Committee (CBNUA-901-15-01) of Chungbuk National University. Mice used herein were obtained from Dahan Biolink (Seoul).

Preparation of Tissue Samples

Lung cells and lung tissues collected from pneumothorax patients who had undergone surgery at Chungbuk National University Hospital (Cheongju-si) were used. In addition, the patients did not show any other pathology in the lungs, and all studies were conducted under the review and approval of the Chungbuk National University Hospital, Clinical Institutional Review Board (2014-02-009-009).

Antibody Preparation

Anti-pFAK (Y576) (#3281, 1:500), FAK (#3258, 1:1,000 for immunoblotting/1:200 for immunohistochemistry), p53 (#2524, 1:1,000), pp53 (S15) (#9284, 1:500), pPAK1(T423) (#2610, 1:500), paxillin (Y118) (#2541, 1:500), and pγH2AX (S139) (#9713, 1:200) antibodies were purchased from Cell Signaling Technology (Danvers, Mass.) and used. In addition, Anti-pFAK (Y397) (611806, 1:500), paxillin (610051, 1:1,000), GIT2 (P94020, 1:1,000), Cdk2 (610145, 1:500), Cdk4 (610147, 1:500), Cyclin D (610279, 1:500), Cyclin E (551159, 1:500), pRB (610884, 1:500), ppRB (610490, 1:500) and p19 (610530, 1:500) antibodies were purchased from BD Biosciences (San Jose, Calif.) and used. Calpain-2 (sc-373966, 1:1000) and calpain-4 (sc-30065, 1:1,000), p16 (sc28260, 1:500 for immunohistochemistry analysis/1:200 for immunohistochemistry analysis), p21 (sc-6246, 1:500), GIT1 (sc-9657, 1:500) and amphiphysin I (sc-376402 and sc-39028, 1:1,000) antibodies were purchased from Santa Cruz Biotechnology (Dallas, Tex.) and used.

In addition, GFP (NB600-308, 1:1,000 for immunoblotting analysis/1:200 for immunohistochemistry analysis) antibody was purchased from Novus Biologicals (Centennial, Colo.) and used. The active integrin β1 (MAB2079Z, 1:50) and GST (A00895, 1:1,000) antibodies were purchased from Merck Millipore (Burlington, Mass.) and Genscript (Piscataway, N.J.) and used, respectively. Anti-β1 integrin antibody (ab30394, 1:50) and 6xHis-tag (ab18184, 1:1,000) antibodies were purchased from Abcam (Cambridge, UK) and used. The Anti-βPIX antibody (1:1,000 for immunoblotting analysis/1:200 for immunohistochemistry analysis) used herein was an antibody to βPIX C-terminal sites (439~648 aa).

Plasmid and DNA Constructs

Figure 7:
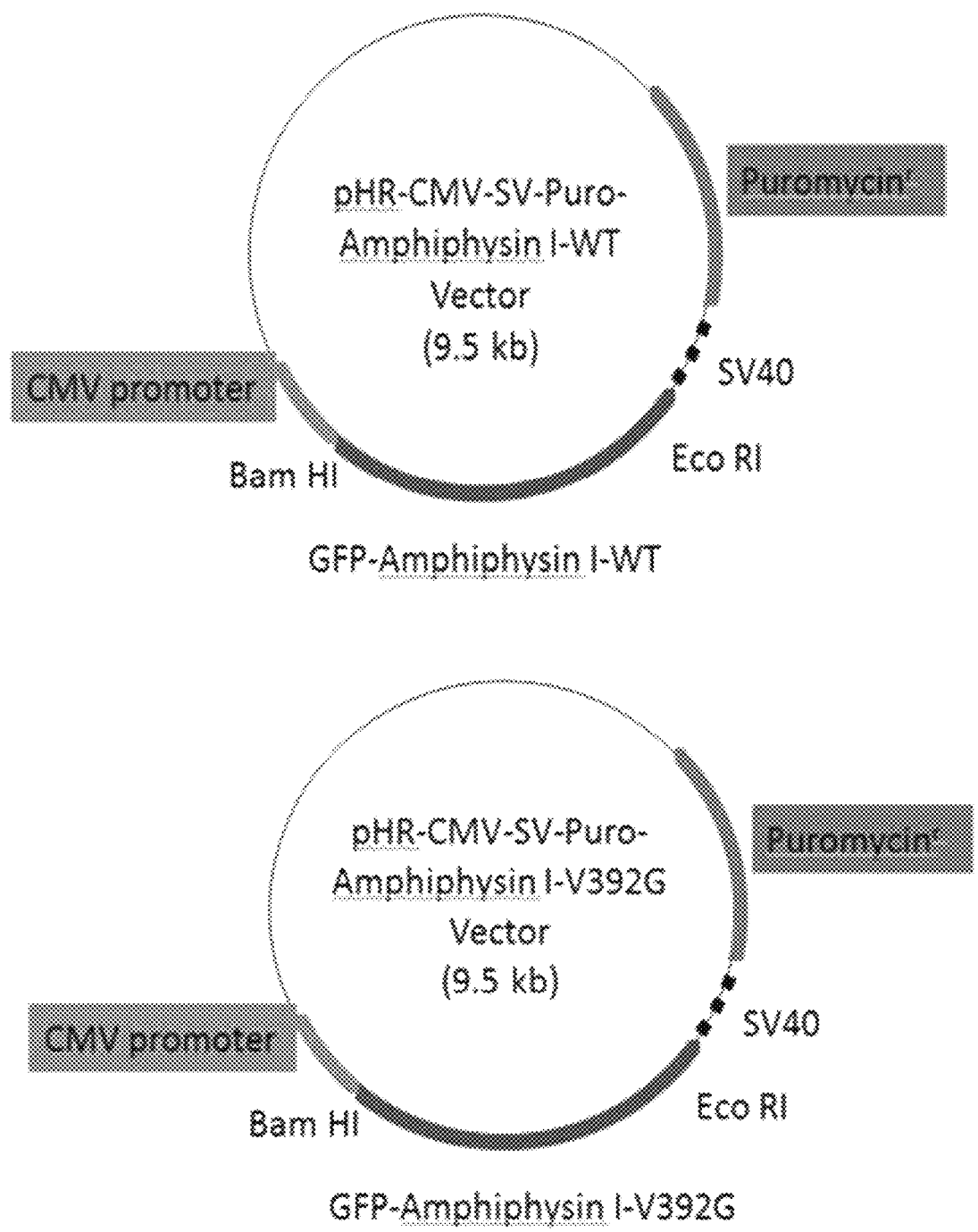
FIG. 7 is a cleavage map of pHR-CMV-SV-Puro-Amphiphysin I-WT and pHR-CMV-SV-Puro-Amphiphysin I-V392G recombinant vectors respectively produced by cloning for overexpression of the amphiphysin-I-WT (wild type) and amphiphysin-I-V392G (mutant) according to an embodiment of the present invention.

The βPIX constructs, si-rPIX (WT) and si-rPIX (DHmt) were cloned into pHR-CMV SV40 for lentiviral expression. Si-rPIX (WT) and si-rPIX mutants were produced using the QuickChange II site-directed mutagenesis kit (Agilent). The N-terminal (NT, aa 1-351) and C-terminal (CT, 346-695) sites of amphiphysin I and calpain-2 were cloned into pGEX4T-1. Wild-type (WT) and mutant (MT (V392G)) of amphiphysin I were cloned into pHR-CMV SV40 for expression in lentivirus. Calpain-2 was cloned into pGEX4T-1. Calpain-2 cDNA was purchased from OriGene and used. The GIT1 C-terminus (CT, aa 376-770) was cloned into the pGEX4T-1 vector for expression in bacteria. The cleavage map of pHR-CMV-SV-Puro-Amphiphysin I-WT and pHR-CMV-SV-Puro-Amphiphysin I-V392G recombinant vectors respectively produced by cloning for overexpression of the amphiphysin-I-WT (wild type) and amphiphysin-I-V392G (mutant) of the present invention is shown in FIG. 7.

In-vivo Delivery of siRNA, Lentivirus, or Transferrin

Mice were anesthetized by intraperitoneal injection of avertin (0.45 mg/g, 2-2-2 tribromo ethanol/body weight) and the incisor teeth of the mice were fixed to a bar on a platform. A 1-inch, 22 gauge Safelet IV catheter equipped with a blunted needle was placed inside the mouth to detect white light emitted from the trachea. The catheter located in the trachea was detected, and the needle was removed from the catheter. Subsequently, Invivofectamine RNAi complex (75 µl liposomes) was prepared according to the manufacturer's protocol, and lentiviral particles or Alexa Fluor 594-transferrin was directly pipetted into the opening in the catheter to deliver siRNA, lentivirus, or transferrin in vivo.

Cell Culture

Human diploid fibroblast (HDF) cells and 293 T cells were incubated in DMEM (Dulbecco's modified Eagle's medium) containing 10% FBS and antibiotics in an incubator maintained at 37° C. and 5% CO2.

β-Galactosidase (SA-β-Gal) Assay

The measurement of senescence-associated β-galactosidase (SA-β-Gal) activity was performed by slightly modifying the method described in Proc. Natl. Acad. Sci. USA 92, 9363-9367 (1995) under a pH of 6.0. Specifically, the cells were washed with phosphate-buffered saline (PBS), fixed with 3% formaldehyde for 5 minutes, and then washed again with PBS. Then, the cells were incubated in SA-β-gal staining solution (Sigma-Aldrich) at 37° C. for 13 to 14 hours and then stained with Hoechst 33258 for 30 minutes to count the number of cells. Cellular senescence was evaluated as the percentage of SA-β-gal-positive cells (blue-stained) to the total number of cells, and for tissues, animals were anesthetized and perfused with saline, after which the tissues were flash-frozen in liquid nitrogen and were embedded with an OCT compound. Then, the tissues were immediately cut to a thickness of 10 µm, fixed with a PBS solution containing 1% formaldehyde, washed with PBS, and incubated in a SA-β-gal staining solution at 37° C. for 13 to 14 hours. Then, the nuclei were stained with safranin-O and analyzed with a Vectashield mounting medium (Vector Laboratories, Inc, Burlingame, Calif.).

Transient Transfection

Transfection using DNA or siRNA was performed using a Lipofectamine 2000 or Lipofectamine RNAiMAX transfection reagent according to the manufacturer's instructions. The cells were plated on a plate coated with fibronectin or a glass cover slip and transfected with the indicated DNA for 1 day and with siRNA for 3 to 4 days.

Immunohistochemistry

The tissues were fixed with 10% neutral buffered formalin, dehydrated, and embedded in paraffin. The paraffin-embedded tissue blocks fixed with formalin were sectioned (to a thickness of 4 µm). After deparaffinization, the slides were subjected to an antigen search procedure in 10 mM sodium citrate buffer (pH 6.0) using a pressure cooker (Decloaking chamber; Biocare Medical) for 10 minutes, and were reacted with a blocking solution (0.3% Triton X-100, 1% bovine serum albumin, 0.05% Tween 20, 0.1% cold-water fish gelatin and 0.05% sodium azide in PBS) at room temperature for 1 hour. Primary antibodies were reacted with each of the sections at 4° C. overnight. Then, the slides were washed 5 times with PBS containing 0.1% Tween 20 and 0.1% BSA, and were each reacted with Alexa Fluor-conjugated secondary antibody (1:200) at room temperature in the dark for 1 hour. Subsequently, the slides were washed several times, stained with Hoechst 33258, and analyzed with Vectashield mounting medium (Vector Laboratories, Inc). For DAB (diaminobenzidine-HCl) staining, the slides were reacted with methanol containing 0.3% hydrogen peroxide at room temperature for 20 minutes to block the intrinsic peroxidase activity before treatment with the blocking solution. Then, the slides were reacted with a biotin-conjugated secondary antibody at room temperature for 30 minutes and finally reacted with peroxidase-conjugated streptavidin at room temperature for 30 minutes. Peroxidase activity was measured using DAB as a substrate, and as a negative control, a section treated only with a TBS solution, and not treated with the primary antibody, was used. The sections were stained with H & E for histological analysis.

Immunocytochemistry

The cells were fixed with 3.7% paraformaldehyde for 15 minutes, permeated with 0.2% Triton X-100 for 5 minutes, and blocked with PBS containing 2% BSA at 25° C. for 30 minutes. For antigen staining, the cells were reacted with a primary antibody at 25° C. for 1 hour and then reacted with a secondary Alexa Fluor-conjugated antibody for 1 hour. For visualization of F-actin, the cells were stained at 25° C. with Alexa Fluor 568-conjugated phalloidin for 30 minutes, and expression of the stained protein was analyzed with Meta-Morph software version 7.1.7 (Molecular Devices).

Immunoblotting and Immunoprecipitation

The cells were lysed in cold lysis buffer (50 mM HEPES, pH 7.5, 150 mM NaCl, 10% glycerol, 1% Triton X-100, 500 μM EDTA, 200 μM sodium pyruvate, 50 mM β-glycerophosphate), and the supernatant was reacted with a primary antibody at 4° C. for 18 hours to perform immunoprecipitation. The immune precipitates were electrophoresed by 8-10% SDS-PAGE and transferred to a polyvinylidene fluoride membrane in a tris-glycine-methanol buffer (25 mM Tris base, 200 mM glycine and 20% methanol). Then, the membrane was blocked with Tris-buffered saline (TBS-T; 50 mM Tris, 150 mM NaCl, 0.1% Tween-20) containing 3% BSA for 30 minutes and reacted at room temperature with the primary antibody for 1 hour, and was then washed 3 times with TBS-T. Subsequently, the membrane was reacted at room temperature using a secondary horseradish-peroxidase-conjugated antibody for 1 hour, and washed 3 times with TBS-T, and then a signal was detected using an enhanced chemiluminescence reagent.

Transferrin Endocytosis

The cells were treated on ice with a cold viable cell imaging solution (LCIS: 140 mM NaCl, 20 mM HEPES, 2.5 mM KCl, 1.8 mM CaCl2, 1.0 mM MgCl2, pH 7.4) containing 20 mM glucose and 1% BSA for 10 minutes. The cells were treated with an LCIS solution containing 20 mM glucose and 1% BSA, and 20 μg/ml of Alexa Fluor 594-transferrin, and reacted therewith at 37° C. for 15 minutes. Then, the cells were washed with PBS and fixed with 4% paraformaldehyde for 10 minutes. In order to analyze transferrin endocytosis in the lungs of mice, 0.1 μM Alexa Fluor 594-Transferrin was inserted directly into the opening of the catheter and delivered into the trachea. After 1 hour, the heart of animals was perfused with PBS to penetrate the same. The tissue was dissected and frozen in liquid nitrogen, immediately sliced to a thickness of 10 μm with a frozen microtome, and fixed with cold acetone for 10 minutes. Each sliced section was stained with DAPI (10 μg/ml) to label the nuclei, and was mounted using Vectashield mounting medium. Endocytotic transferrin was observed with an Olympus FluoView confocal microscope (FV10i, Olympus, Japan) or a fluorescence microscope (DP30BW, Olympus, Japan), and the fluorescence intensity was analyzed with ImageJ software.

Integrin β1 Endocytosis

Starved cells were pretreated with 10 μM of nocodazole for 20 minutes, and treated and reacted with an anti-active β1 integrin antibody (1:200) at 37° C. for 40 minutes. Then, unbound antibody and nocodazole were washed with PBS, followed by tracking for 60 minutes. Then, the cells were washed with warm PBS, and surface antibodies were removed with an acid rinse (0.5% acetic acid, 0.5 M NaCl, pH 3.0). The cells were fixed with 4% paraformaldehyde and permeated with 0.2% Tween 20. The endocytotic β1 integrin was reacted with Alexa Fluor-conjugated secondary antibody (1:200) for 1 hour and then analyzed.

Statistical Analysis

All data were represented as mean ±SEM. Representative data were analyzed from at least three independent experiments. Statistical significance was assessed using a Student's t-test and a Wilcoxon Mann-Whitney test using Sigma Plot for Windows (version 12). P<0.05 was considered statistically significant.

EXAMPLE 1

Analysis of Expression Level of βPIX in Aged Tissues and Cells

The present inventors collected lung, kidney, spleen, heart and skin tissues from 3-, 15- and 24-month-old mice undergoing aging in order to determine whether or not changes in the expression level of the βPIX protein occur depending on the aging process, and then detected the level of βPIX expressed in the tissue through immunoblotting and immunohistochemical staining. The results showed that the levels of βPIX expressed in tissues of old mice (lungs, kidneys, spleen, heart, and skin) were remarkably reduced compared to that of young mice (see FIG. 1A).

In addition, in order to detect the same in greater more detail, the expression of βPIX and p16 proteins, known as aging indicators, from lung tissue of young mice (3 months old) and old mice (24 months old) was analyzed by immunohistochemical staining. The result showed that the expression of βPIX was remarkably reduced in the lungs of old mice compared to the lungs of young mice, whereas the expression of p16, an indicator of aging, was increased in old mice (see FIGS. 1B and 1C). The same results as above were obtained from analysis of the expression levels of βPIX and p16 proteins in lung tissue obtained from the lungs of a young subject (14 years old) and an elderly subject (73 years old) by immunohistochemical staining. This showed that the expression of βPIX was decreased, but the level of p16 protein was increased in lung tissues of elderly subjects (FIGS. 1D and 1E).

In addition, in order to detect whether or not the same results as above are obtained in cells, as well as tissues, the expression levels of βPIX and p16 in young-passage human dermal fibroblasts cells and old-passage human dermal fibroblasts cells were measured. The result showed that the expression of βPIX in old HDF cells was decreased compared to that of young HDF cells, whereas the expression of p16 in old HDF cells was increased compared to that of young HDF cells, and SA-β-gal (senescence-associated β-galactosidase) activity as another known aging indicator was also increased in old HDF cells (see FIGS. 1F to 1H).

Therefore, it can be seen that the expression of βPIX decreased as aging progressed and that the decrease in the expression of βPIX was closely associated with senescence.

EXAMPLE 2

Reduction of Integrin β1 and Transferrin Endocytosis by Suppressed βPIX Expression As can be seen from Example 1, when aging occurs, the expression of βPIX is reduced. Accordingly, the present inventors endeavored to determine through the following experiment whether or not the action of endocytosis is reduced by the aging mechanism caused by the decrease in the expression of βPIX. That is, in order to determine how integrin β1, which regulates cell adhesion when suppressing βPIX expression, affects endocytosis, dermal fibroblasts (HDF) were treated with βPIX siRNA and nocodazole, cultured and reacted with an antibody of active integrin β1, and the endocytotic integrin β1 was analyzed through a staining method using the integrin β1 antibody.

In addition, in order to analyze the effect of suppressed βPIX expression on transferrin endocytosis, skin fibroblasts (HDF) were treated with siRNA for βPIX, and were further treated and reacted with an LCIS solution and Alexa Fluor 594-transferrin. Endocytotic transferrin was observed with an Olympus FluoView confocal microscope (FV10i, Olympus, Japan) or a fluorescence microscope (DP30BW, Olympus, Japan), and the fluorescence intensity was analyzed using ImageJ software. In addition, in order to analyze transferrin endocytosis in mouse lung tissue, Alexa Fluor 594-transferrin was directly inserted into the opening of the catheter and delivered to the trachea, and the lung tissue was sliced, stained using a transferrin antibody, and observed with a confocal microscope or a fluorescence microscope.

In addition, the siRNAs used to suppress βPIX expression are as follows.

```
siPIX1:
5'-UCAACUGGUAGUAAGAGCAAAGUUU-3' siPIX2:
5'-UUGAGCUGCAGAUCCUGACGGAAGC-3' siCtrl:
5'-CCUACGCCACCAAUUUCGU-3' siPIXm1:
5'-CCAACUGGUAGUACGAGCCAAGUUU-3' siPIXm2:
5'-GAGGACCUAGGAGAGUUCAUGGAAA-3'
```

Endocytosis of integrin β1, which regulates cell adhesion, in HDF cell lines was detected. The result showed that endocytosis of integrin β1 was remarkably reduced in the group in which βPIX expression was suppressed (siCtrl-treated group) compared to the group in which βPIX expression was not suppressed (see FIGS. 2A and 2B), and that endocytosis of transferrin, which is a typical endocytosis indicator protein, was remarkably reduced in the group in which the expression of βPIX was suppressed (see FIGS. 2C and 2D). In addition, the same result as above was obtained in the lung tissue of the mice injected with siRNA of βPIX, and the endocytosis of transferrin was reduced in the tissues in which βPIX expression was suppressed (see FIGS. 2E and 2F).

Therefore, these results proved that suppression of the expression of βPIX can promote senescence and that the action of endocytosis decreases when senescence occurs.

EXAMPLE 3

Detection of Amphiphysin-I (AMPH-I) Cleavage Induced by Senescence

Figure 3B:
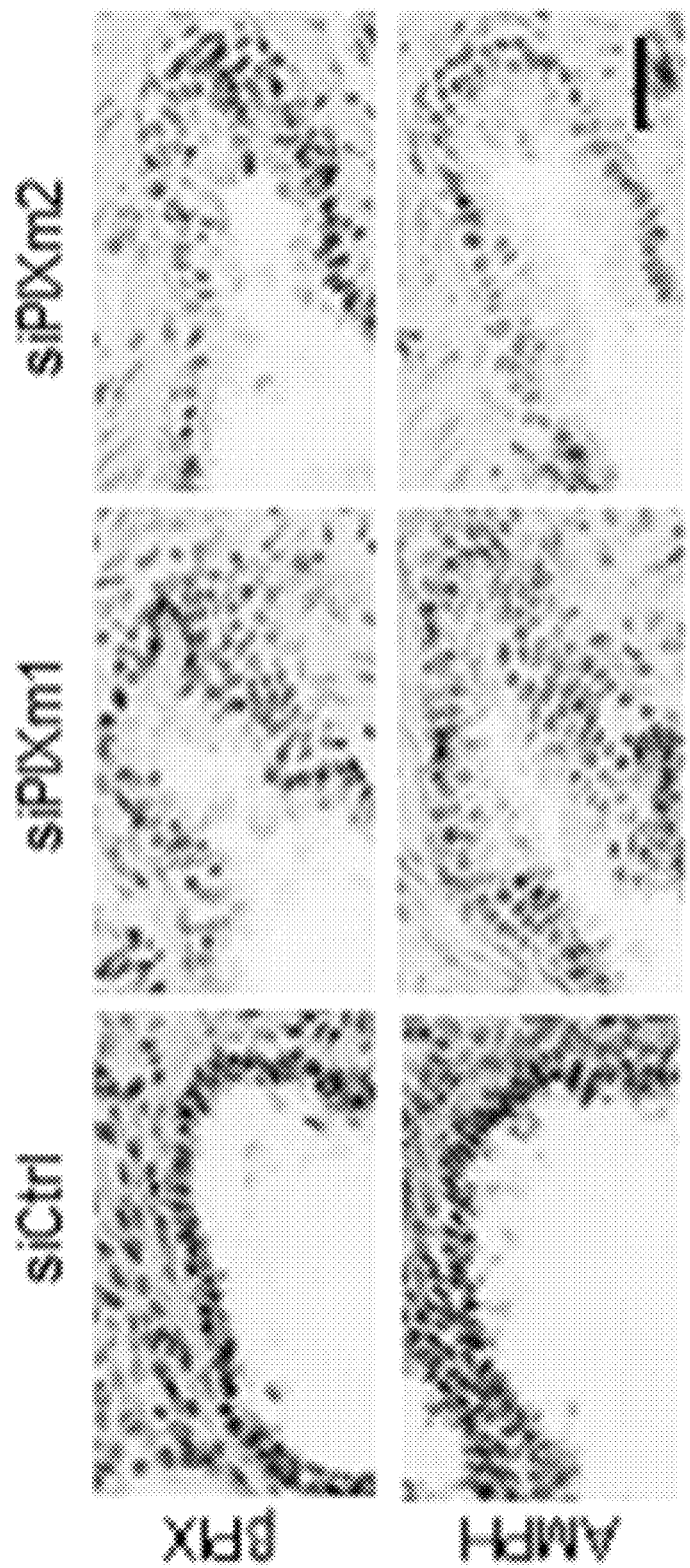
FIG. 3B is an image showing the result of immunohistochemistry showing the expression levels of βPIX and AMPH in the lung tissue of mice treated with βPIX siRNA.
Figure 3C:
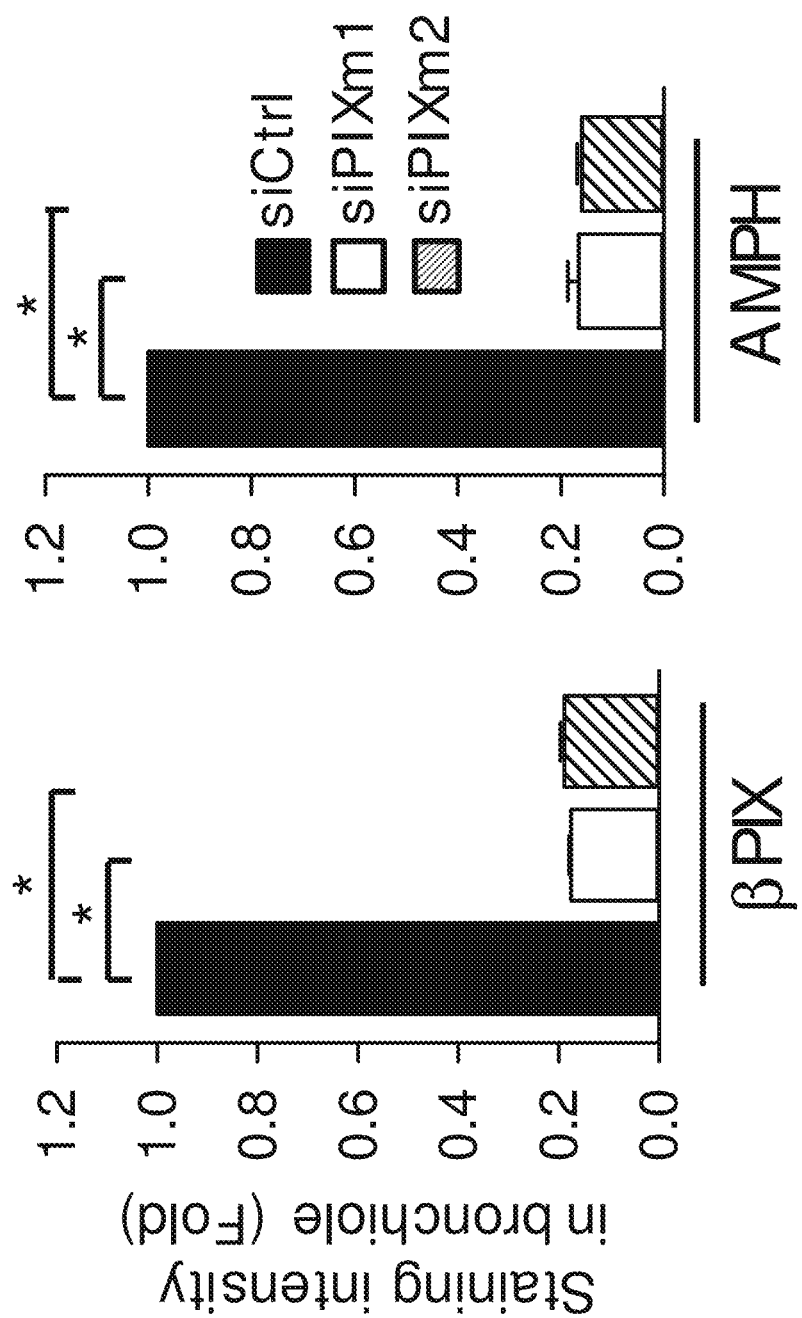
FIG. 3C is a bar graph showing the quantitative measurement of the result of FIG. 3B.
Figure 3D:
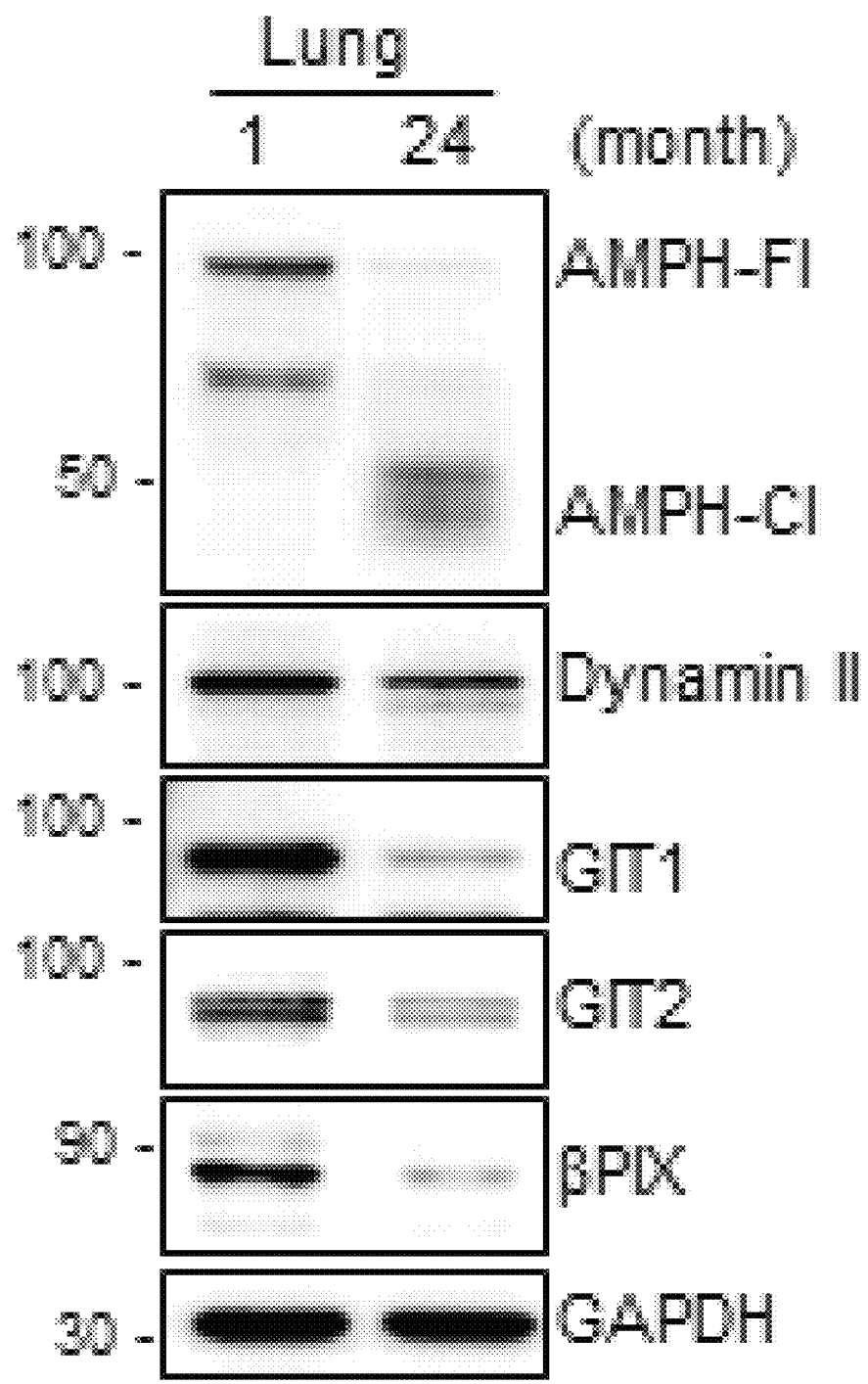
FIG. 3D shows the result of immunoblotting analysis showing whether or not cleavage of AMPH-I occurs in 1-month-old young mice and 24-month-old mice.
Figure 3E:
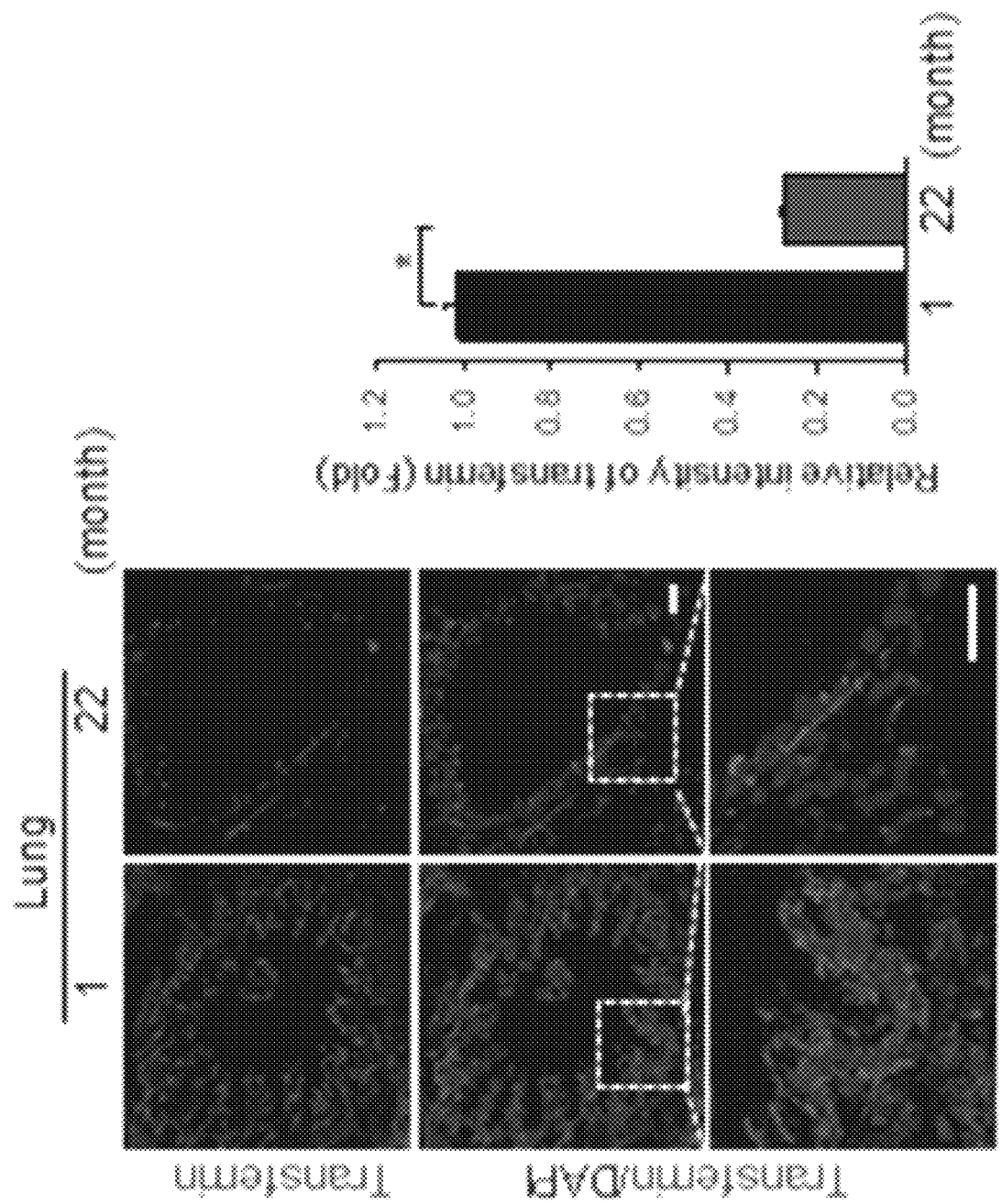
FIG. 3E is a confocal microscopy image showing the degree of transferrin endocytosis in the lungs of 1-month-old young mice and 22-month-old mice and a graph showing the result of quantitative analysis.

It can be seen from the results of Example 2 above that endocytosis is reduced when senescence occurs. Thus, the present inventors attempted to determine the mechanism of action that the expression of βPIX regulates in relation to senescence. For this purpose, HDF cells were treated with βPIX siRNA to suppress the expression of βPIX, and then changes in the expression patterns of endocytosis regulatory proteins were analyzed through immunoblotting. Among the proteins involved in endocytosis, the AMPH-C1 fragment, from which the C-terminal site (about 50 kDa) in amphiphysin (AMPH)-I was cleaved through the suppression of the expression of βPIX, was detected. Meanwhile, the AMPH-C1 fragment in which the C-terminus was cleaved was not observed in the group in which the expression of βPIX was not suppressed. In addition, dynamin II protein, which is another regulatory protein for endocytosis, did not undergo cleavage like proteins such as amphiphysin 1 even when βPIX was expressed (see FIG. 3A). In addition, the result of experiments performed on the lung tissue of mice showed that the expression of amphiphysin-I (AMPH-I) was decreased in the lungs of the mice in which the expression of βPIX was suppressed compared to the control group (FIGS. 3B and 3C).

Furthermore, in order to verify senescence and C-terminal cleavage of AMPH-I, the present inventors obtained lungs from young mice (1 month old) and old mice (22 months/24 months old), detected the expression levels of AMPH-I and βPIX proteins through immunoblotting, and observed changes in transferrin endocytosis. As a result, AMPH C-terminal fragments sectioned due to AMPH-I cleavage were detected in the lungs of old mice, whereas AMPH C-terminal fragments were not detected in the young mice (see FIG. 3D). In addition, it was found that the expression of the βPIX/GIT complex was decreased in the lungs of old mice, and the endocytosis of transferrin was also remarkably reduced in the lungs of old mice compared to the lungs of young mice (see FIG. 3E).

Based on these results, the present inventors found that, when βPIX expression is decreased (suppressed), senescence proceeds, and this senescence progress reduces the action of endocytosis by cleavage (C-terminal) of AMPH.

EXAMPLE 4

Identification of Site of Amphiphysin-I (AMPH-I) Cleavage Induced by Senescence

It can be seen from Example 3 that the C-terminus of amphiphysin-I (AMPH-I) was cleaved in the process of promoting aging through suppression of βPIX expression. Accordingly, the present inventors conducted an experiment to identify an effector that cleaves the C-terminus of AMPH-I and a specific cleaved amino acid site during aging. Calpain is an intracellular protease that is activated by calcium ions, and acts to limitedly degrade proteins adjacent to the cell membrane or cytoskeleton and proteins involved in cell signaling, and AMPH-I is known to act as a substrate for calpain-2. Accordingly, the present inventors selected three target sites (serine at position 333 (S333), serine at position 377 (S377) and valine at position 392 (V392) in the AMPH-I amino acid sequence) in AMPH-I, on which calpain-2, a protease, is predicted to act, and then produced AMPH-S333G, AMPH-S377G, and AMPH-V392G mutants by substituting each of the corresponding amino acids with a glycine (G). The mutants were each produced with AMPH-I-wild type (WT) as a template using a point mutation kit (QuikChange II Site-Directed Mutagenesis Kit, Stratagene) (see FIG. 4A). 293T cells were transfected with expression vectors containing three types of AMPH-1 mutants, and whether or not AMPH-I was cleaved was detected depending on treatment with ionomycin, which can induce the activation of calpain. As shown in FIG. 4B, the result showed that among the three mutants, only the AMPH-V392G mutant was not cleaved by the activated calpain (FIG. 4B).

Based on this result, the present inventors found that the position of AMPH-I cleaved by activated calpain-2 was the amino acid serine 392 (S392) position, and the mutant AMPH-V392G produced by substitution of this position was not cleaved.

EXAMPLE 5

Figure 5A:
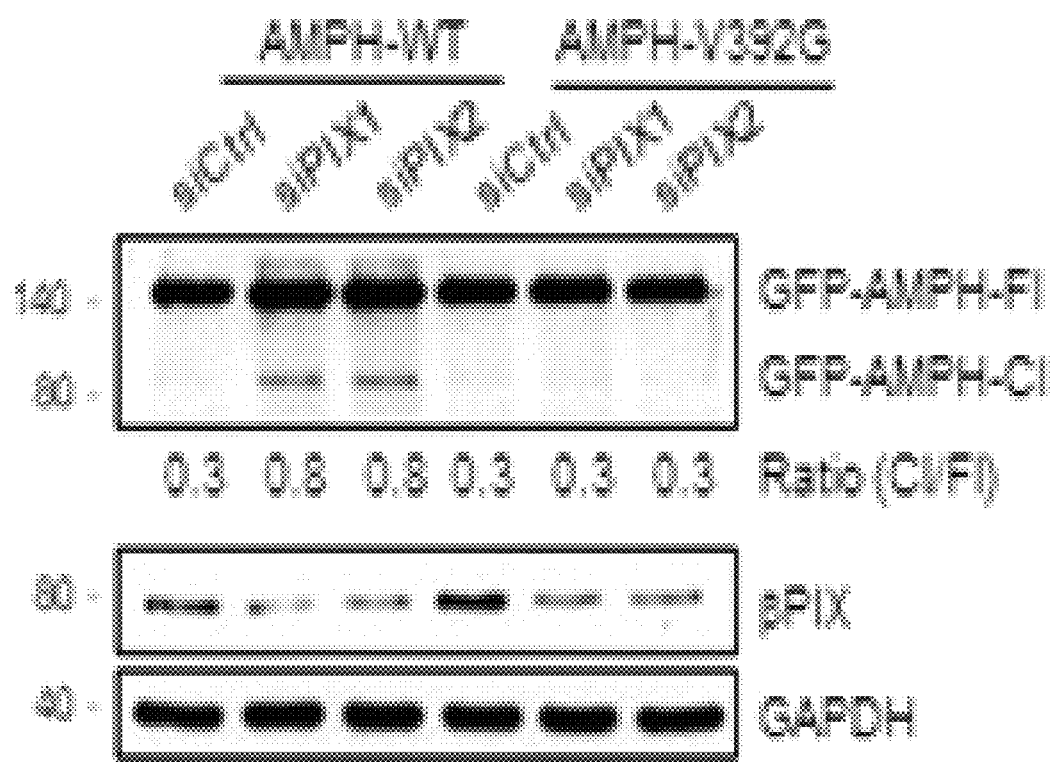
FIG. 5A shows the result of immunoblotting for detecting cleavage of AMPH-WT and AMPH-V392G (mutant that impedes calpain-mediated cleavage) in HDF cells in which βPIX expression was suppressed by treatment with βPIX siRNA (HDF cells undergoing senescence caused by suppressed βPIX)
Figure 5B:
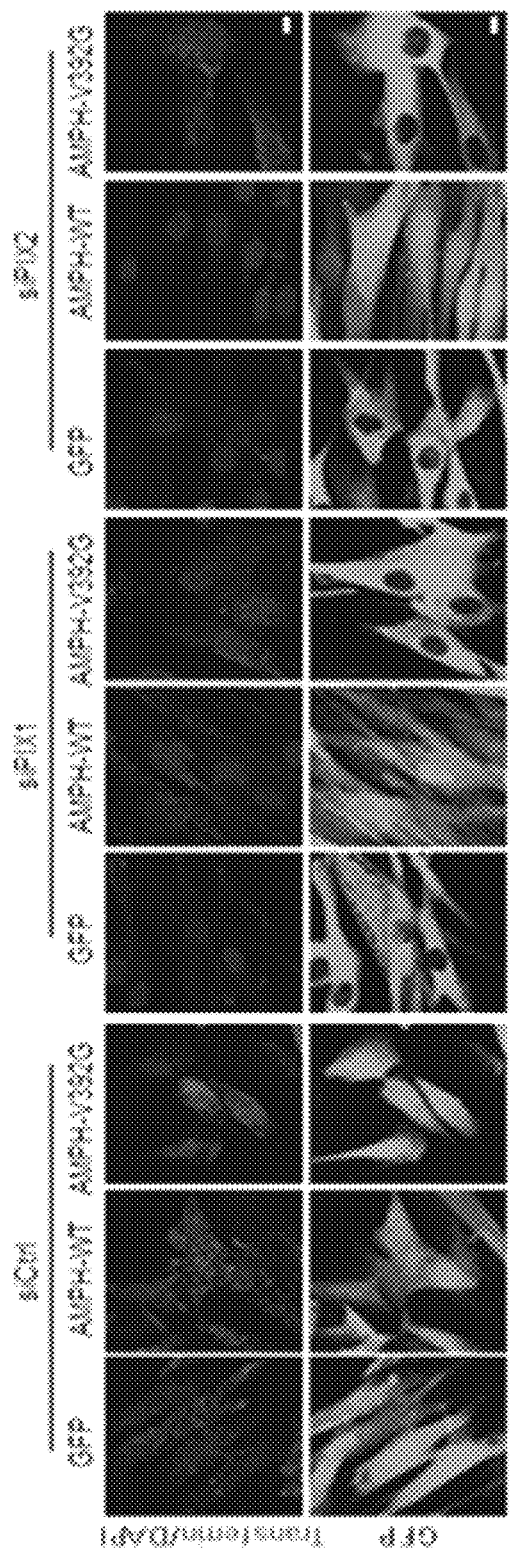
FIG. 5B is a confocal microscope image showing the degree of endocytosis of transferrin after treatment of HDF cells, in which βPIX expression is suppressed, with AMPH1-WT and AMPH-V392G.
Figure 5C:
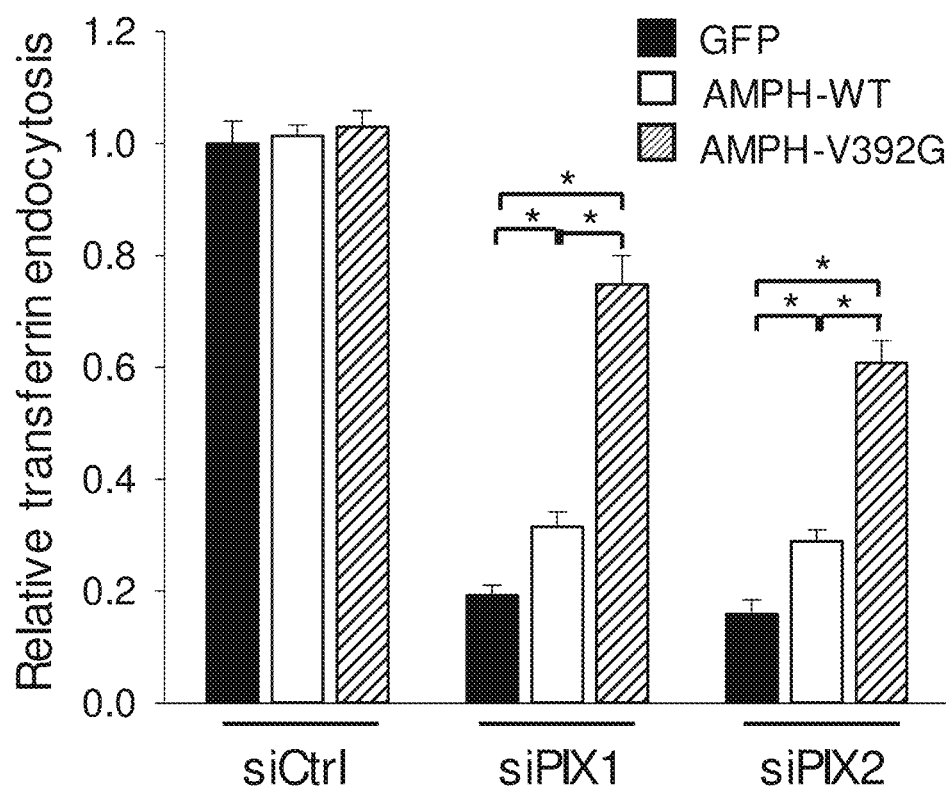
FIG. 5C shows the result of quantitative measurement of the degree of transferrin endocytosis in the experimental group of FIG. 5B.
Figure 5D:
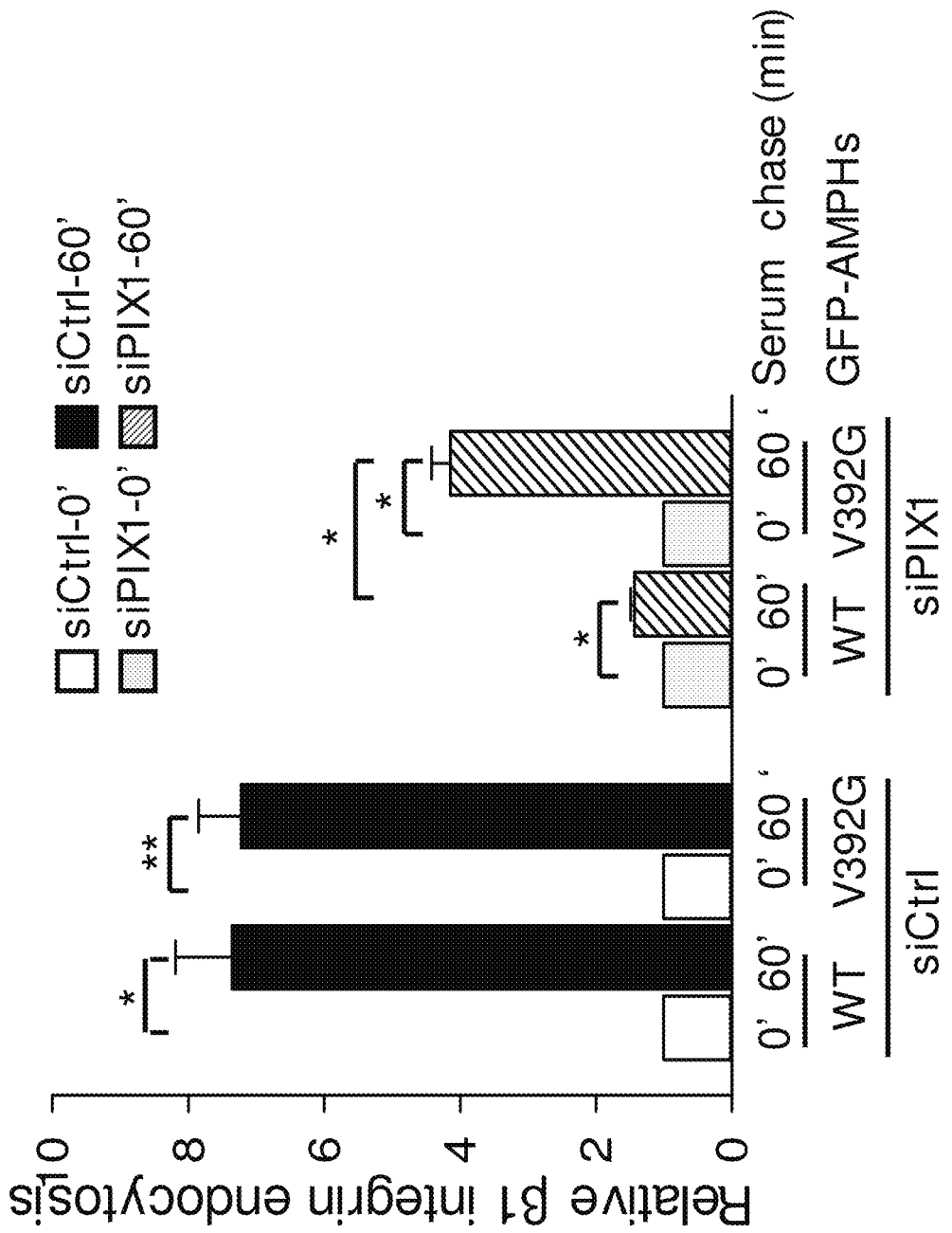
FIG. 5D shows the degree of endocytosis of a β1 integrin.

Analysis of Effect of AMPH-V392G Mutant on Reduction of Endocytosis and Promotion of Cellular Senescence Induced by Suppressed βPIX Expression In order to detect the functions of the AMPH-V392G mutant according to the present invention in relation to the reduction of endocytosis and promotion of senescence induced by suppressed βPIX expression, HDF cell lines were transfected with each of the AMPH-WT and AMPH-V392G mutant to induce expression thereof in cells, and treated with βPIX siRNA to suppress the expression of βPIX, and whether or not cleavage of the AMPH-I protein occurred was determined through immunoblotting. As shown in FIG. 5A, the result showed that cleavage of the AMPH-I protein induced by suppression of βPIX expression did not occur in the AMPH-V392G mutant of the present invention. This means that the AMPH-V392G mutation of the present invention is closely associated with the inhibition of endocytosis and the promotion of senescence induced by the suppression of βPIX expression. In this regard, the present inventors observed the effects of treatment of HDF cells having suppressed βPIX expression with AMPH-WT and AMPH-V392G mutant on endocytosis of transferrin and integrin β1. As a result, when the expression of βPIX was suppressed by treatment with siPIX, AMPH-WT remarkably reduced endocytosis, whereas the group treated with the AMPH1-V392G mutant did not reduce endocytosis transferrin and integrin β1 (see FIGS. 5B to 5D).

Figure 5E:
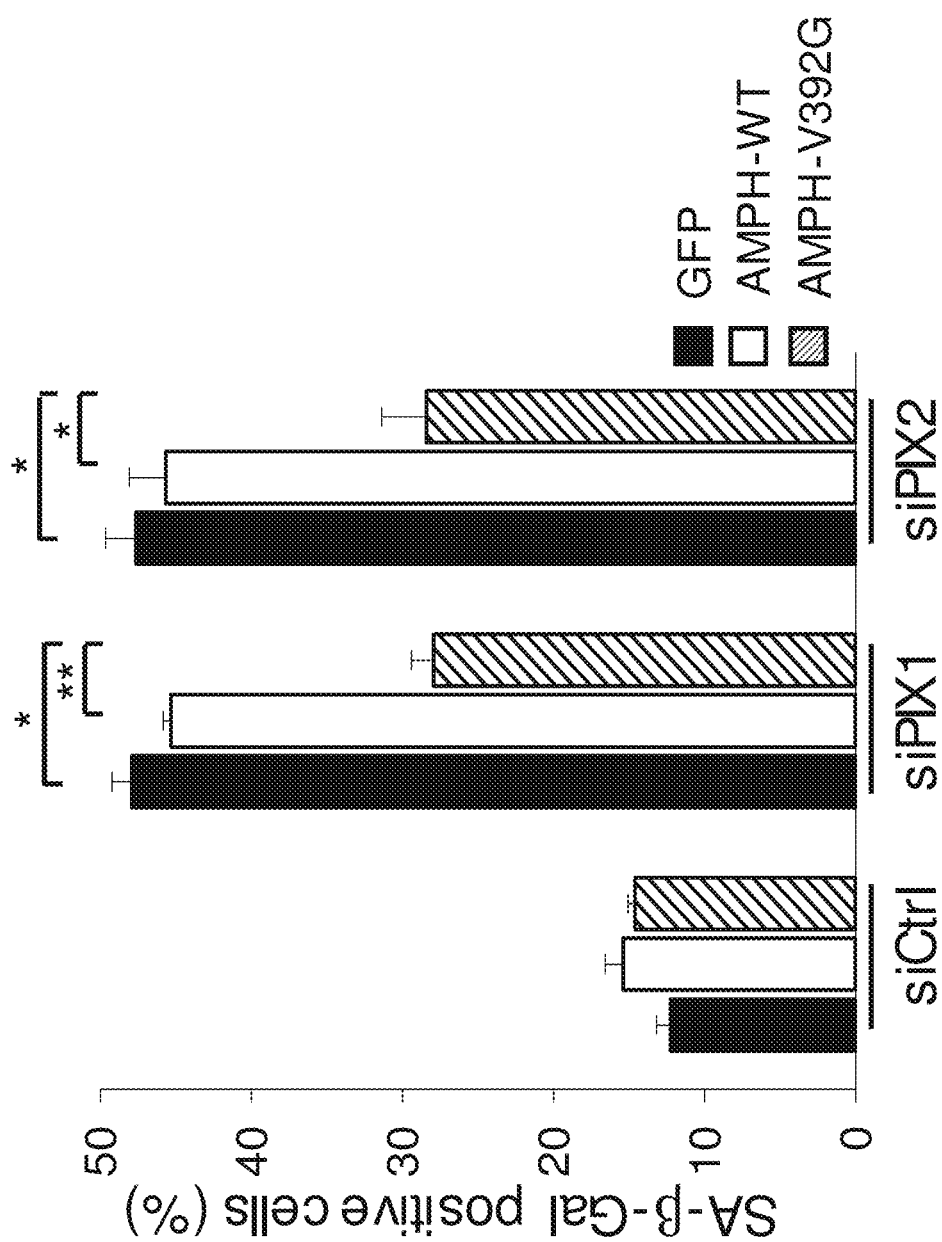
FIG. 5E shows the degree of endocytosis of SA-β-gal positive cell line, an indicator of senescence.

Furthermore, in order to detect whether or not the mutant of the present invention can suppress senescence caused by suppressed βPIX expression, the enzymatic activity of SA-β-gal of each of experimental groups used for the experiment was measured. As shown in FIG. 5E, the result showed that the group treated with the AMPH-V392G mutant had remarkably reduced enzymatic activity of SA-β-gal, a known senescence indicator.

Based on these results, the present inventors found that the senescence phenomenon caused by suppressed βPIX expression is closely associated with endocytosis, and that the reason therefor is that the 392nd valine residue of AMPH-I is cleaved by calpain-2, and the mutant (AMPH-V392G), in which the 392nd valine of AMPH-I is substituted with a glycine residue, designed to prevent the calpain-2-mediated cleavage, can suppress senescence induced by suppressed βPIX expression.

EXAMPLE 6

Analysis of Cellular Senescence Suppression Activity of AMPH-V392G Mutant

Figure 6A:
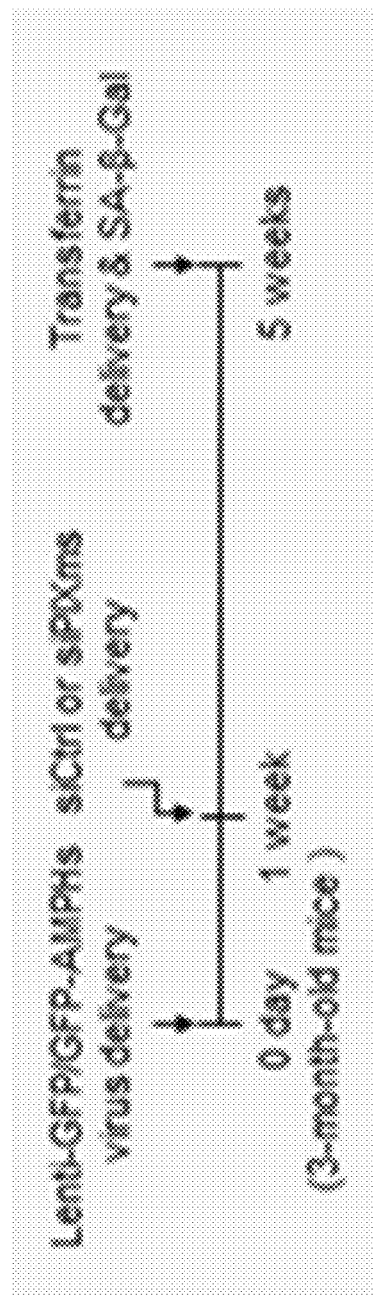
FIG. 6A shows a schematic diagram of an experimental schedule.
Figure 6B:
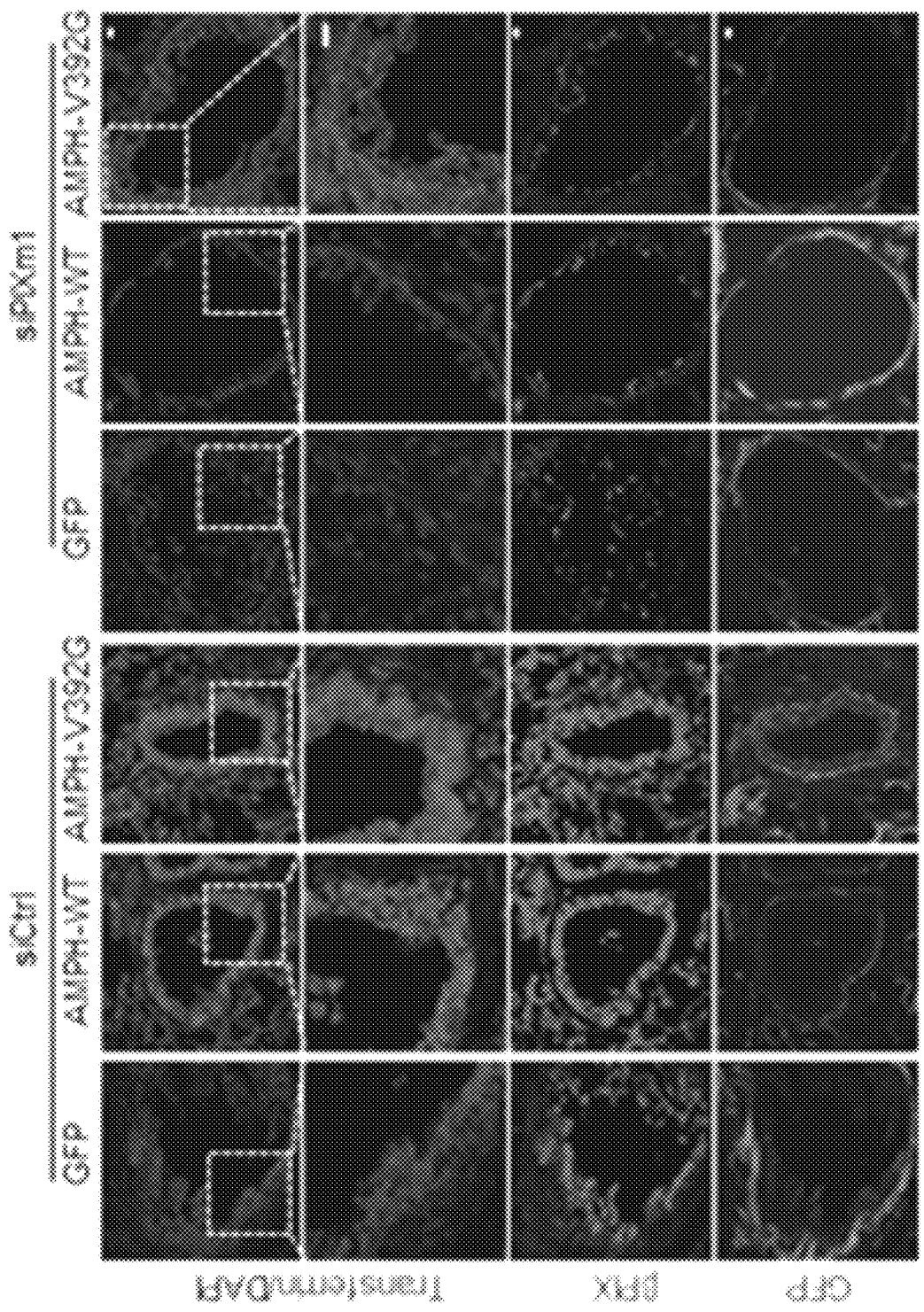
FIG. 6B is a fluorescence microscope image showing the degree of endocytosis of transferrin in the lung tissues of mice injected with βPIX siRNA and siCtrl (a control) after injection of AMPH1-WT and AMPH1-V392G mutant into the lung tissues.
Figure 6C:
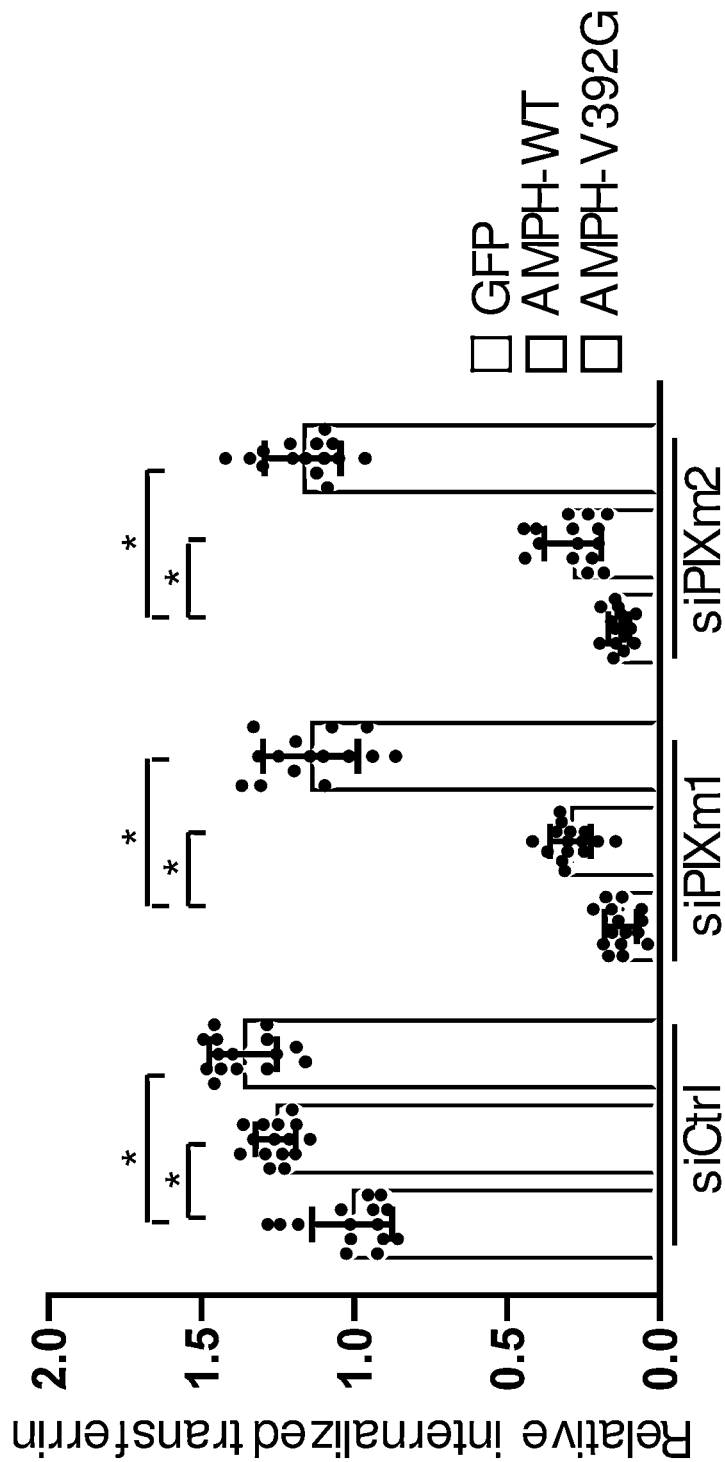
FIG. 6C shows the result of quantitative measurement of the degree of endocytosis of transferrin.
Figure 6D:
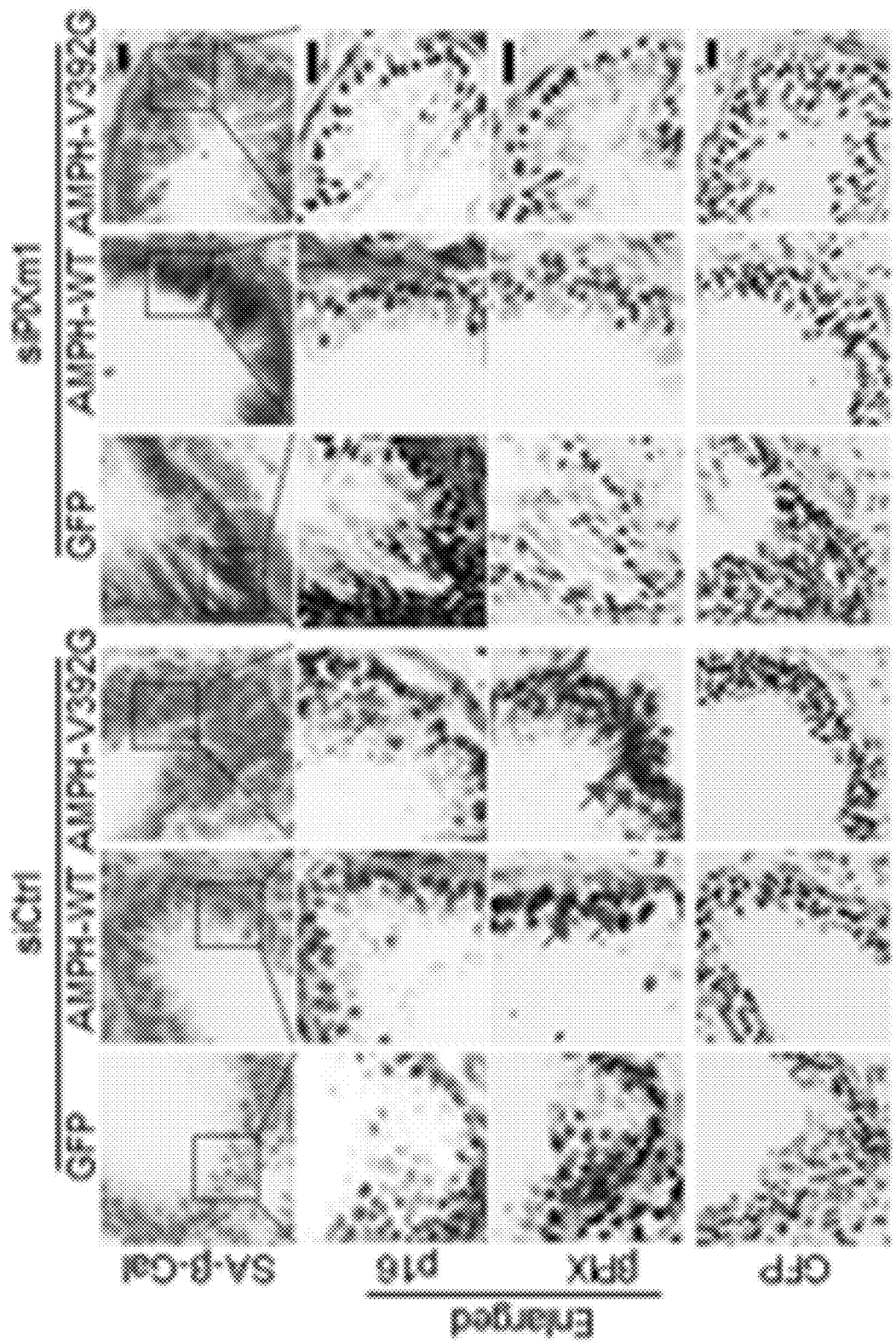
FIG. 6D shows the result of immunohistostaining analysis on p16 expression and SA-β-gal activity, known as senescence indicators, after injection of GFP, AMPH-WT and AMPH-V392G mutant into the lung tissues of mice each introduced with βPIX siRNA and siCtrl (control)
Figure 6E:
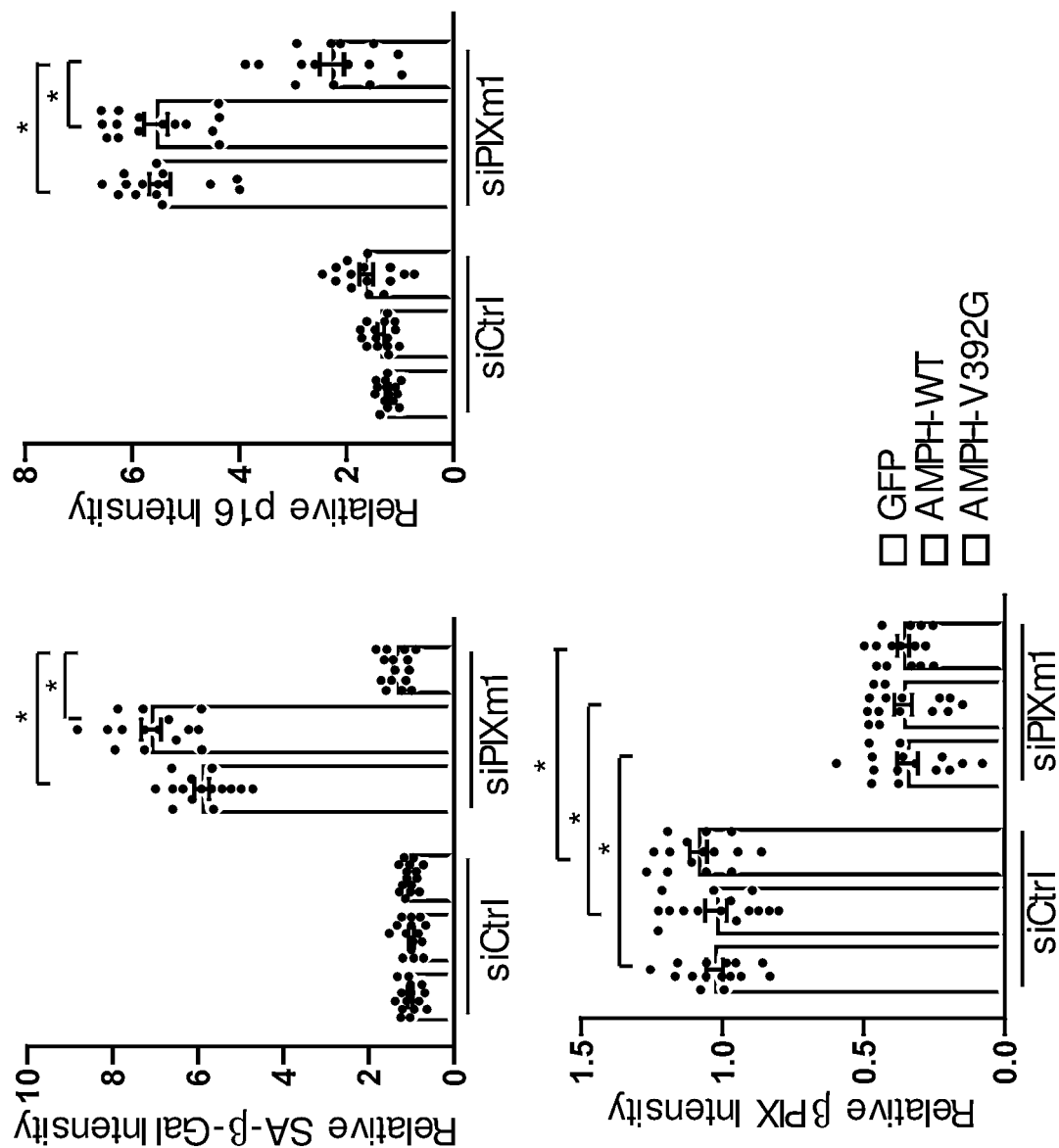
FIG. 6E is a bar graph showing the result of quantitatively measurement of SA-β-gal activity and the expression levels of p16 and βPIX.

In order to identify the effect of suppressing cellular senescence by the AMPH1-V392G mutant identified in Example 5 in an in-vivo animal model, the lungs of mice were primarily infected with AMPH-WT and AMPH-V392G lentiviruses, followed by treatment with siRNA of βPIX to induce senescence of lung tissue by suppressed βPIX expression. This experimental procedure is shown in FIG. 6A. The result of the experiment under the above conditions showed that the effect of suppressing endocytosis was reduced in lung tissue expressing AMPH-V392G, the mutant of the present invention, compared to lung tissue expressing AMPH-WT, even if βPIX expression was suppressed (FIGS. 6B and 6C), and SA-β-gal activity and p16 expression, which are indicators of cellular senescence, were remarkably reduced (FIGS. 6D and 6E).

These results mean that cleavage of the V392 position of AMPH-I in the cellular senescence induced by suppressed βPIX expression induces the suppression of endocytosis and promotion of senescence, and the mutant AMPH-V392G designed to prevent cleavage of the V392 site of AMPH-I according to the present invention by calpain can inhibit the reduction of endocytosis and the promotion of senescence induced by suppressed βPIX expression. Therefore, the present inventors found that the AMPH-V392G mutant of the present invention can be used to regulate senescence.

The amphiphysin-I mutant according to the present invention is capable of suppressing both promotion of cellular senescence and reduction of endocytosis caused by suppression of expression of βPIX (PAK1-interacting exchange factor beta), of preventing cleavage of the amphiphysin-I protein caused by calpain, a protease involved in cellular senescence caused by suppressed βPIX expression, and of suppressing the expression of cellular senescence indicators. Thus, the amphiphysin-I mutant of the present invention is effectively used as a therapeutic agent for senescence or senescence-associated diseases.

Although the preferred embodiments of the present invention have been disclosed, those skilled in the art will appreciate that various modifications, additions and substitutions are possible, without departing from the scope and spirit of the invention as disclosed in the accompanying claims. Therefore, the disclosed embodiments should be considered from an illustrative point of view rather than a limiting point of view. The scope of the present invention is defined by the claims rather than the aforementioned description, and all differences falling within the scope of equivalents thereto should be construed as falling within the scope of the present invention.

What is claimed is:

1. An amphiphysin-I mutant (AMPH-I) comprising a peptide sequence of SEQ ID NO: 1, wherein the 392nd amino acid valine (V) of SEQ ID NO: 1 is substituted with glycine (G).

2. A composition for suppressing, aging and cellular senescence induced by suppression of expression of βPIX (PAK1-interacting exchange factor beta) comprising the amphiphysin-I mutant according to claim 1 as an active ingredient.

3. The composition according to claim 2, wherein the amphiphysin-I mutant suppresses aging and cellular senescence caused by suppression of expression of βPIX (PAK1-interacting exchange factor beta), and suppresses inhibition of endocytosis.

4. The composition according to claim 2, wherein the amphiphysin-I mutant is not cleaved by a calpain at amino acid residue position 392.

5. An amphiphysin-I mutant (AMPH-I) comprising a peptide sequence of SEQ ID NO: 2.

* * * * *

SEQUENCE LISTING

```
<160> NUMBER OF SEQ ID NOS: 2

<210> SEQ ID NO 1
<211> LENGTH: 695
<212> TYPE: PRT
<213> ORGANISM: Artificial Sequence
<220> FEATURE:
<223> OTHER INFORMATION: AMPH1 WT amino acid sequence

<400> SEQUENCE: 1

Met Ala Asp Ile Lys Thr Gly Ile Phe Ala Lys Asn Val Gln Lys Arg
1               5                   10                  15

Leu Asn Arg Ala Gln Glu Lys Val Leu Gln Lys Leu Gly Lys Ala Asp
                20                  25                  30

Glu Thr Lys Asp Glu Gln Phe Glu Glu Tyr Val Gln Asn Phe Lys Arg
            35                  40                  45

Gln Glu Ala Glu Gly Thr Arg Leu Gln Arg Glu Leu Arg Gly Tyr Leu
        50                  55                  60
```

-continued

Ala Ala Ile Lys Gly Met Gln Glu Ala Ser Met Lys Leu Thr Glu Ser
65                  70                  75                  80

Leu His Glu Val Tyr Glu Pro Asp Trp Tyr Gly Arg Glu Asp Val Lys
                85                  90                  95

Met Val Gly Lys Cys Asp Val Leu Trp Glu Asp Phe His Gln Lys
            100                 105                 110

Leu Val Asp Gly Ser Leu Leu Thr Leu Asp Thr Tyr Leu Gly Gln Phe
            115                 120                 125

Pro Asp Ile Lys Asn Arg Ile Ala Lys Arg Ser Arg Lys Leu Val Asp
        130                 135                 140

Tyr Asp Ser Ala Arg His His Leu Glu Ala Leu Gln Ser Ser Lys Arg
145                 150                 155                 160

Lys Asp Glu Ser Arg Ile Ser Lys Ala Glu Glu Phe Gln Lys Ala
                165                 170                 175

Gln Lys Val Phe Glu Glu Phe Asn Val Asp Leu Gln Glu Glu Leu Pro
            180                 185                 190

Ser Leu Trp Ser Arg Arg Val Gly Phe Tyr Val Asn Thr Phe Lys Asn
        195                 200                 205

Val Ser Ser Leu Glu Ala Lys Phe His Lys Glu Ile Ala Val Leu Cys
210                 215                 220

His Lys Leu Tyr Glu Val Met Thr Lys Leu Gly Asp Gln His Ala Asp
225                 230                 235                 240

Lys Ala Phe Thr Ile Gln Gly Ala Pro Ser Asp Ser Gly Pro Leu Arg
                245                 250                 255

Ile Ala Lys Thr Pro Ser Pro Glu Glu Pro Ser Pro Leu Pro Ser
            260                 265                 270

Pro Thr Ala Ser Pro Asn His Thr Leu Ala Pro Ala Ser Pro Ala Pro
        275                 280                 285

Ala Arg Pro Arg Ser Pro Ser Gln Thr Arg Lys Gly Pro Pro Val Pro
    290                 295                 300

Pro Leu Pro Lys Val Thr Pro Thr Lys Glu Leu Gln Gln Glu Asn Ile
305                 310                 315                 320

Ile Ser Phe Phe Glu Asp Asn Phe Val Pro Glu Ile Ser Val Thr Thr
                325                 330                 335

Pro Ser Gln Asn Glu Val Pro Glu Val Lys Lys Glu Thr Leu Leu
            340                 345                 350

Asp Leu Asp Phe Asp Pro Phe Lys Pro Glu Val Thr Pro Ala Gly Ser
        355                 360                 365

Ala Gly Val Thr His Ser Pro Met Ser Gln Thr Leu Pro Trp Asp Leu
370                 375                 380

Trp Thr Thr Ser Thr Asp Leu Val Gln Pro Ala Ser Gly Gly Ser Phe
385                 390                 395                 400

Asn Gly Phe Thr Gln Pro Gln Asp Thr Ser Leu Phe Thr Met Gln Thr
                405                 410                 415

Asp Gln Ser Met Ile Cys Asn Leu Ala Glu Ser Glu Gln Ala Pro Pro
            420                 425                 430

Thr Glu Pro Lys Ala Glu Pro Leu Ala Ala Val Thr Pro Ala Val
        435                 440                 445

Gly Leu Asp Leu Gly Met Asp Thr Arg Ala Glu Glu Pro Val Glu Glu
    450                 455                 460

Ala Val Ile Ile Pro Gly Ala Asp Ala Asp Ala Ala Val Gly Thr Leu
465                 470                 475                 480

```
Val Ser Ala Ala Glu Gly Ala Pro Gly Glu Ala Glu Ala Glu Lys
                485                 490                 495

Ala Thr Val Pro Ala Gly Glu Gly Val Ser Leu Glu Gly Ala Lys Ile
            500                 505                 510

Gly Thr Glu Thr Thr Glu Gly Ala Glu Ser Ala Gln Pro Glu Ala Glu
            515                 520                 525

Glu Leu Glu Ala Thr Val Pro Gln Glu Lys Val Ile Pro Ser Val Val
        530                 535                 540

Ile Glu Pro Ala Ser Asn His Glu Glu Gly Glu Asn Glu Ile Thr
545                 550                 555                 560

Ile Gly Ala Glu Pro Lys Glu Thr Thr Glu Asp Ala Ala Pro Pro Gly
                565                 570                 575

Pro Thr Ser Glu Thr Pro Glu Leu Ala Thr Glu Gln Lys Pro Ile Gln
            580                 585                 590

Asp Pro Gln Pro Thr Pro Ser Ala Pro Ala Met Gly Ala Ala Asp Gln
        595                 600                 605

Leu Ala Ser Ala Arg Glu Ala Ser Gln Glu Leu Pro Pro Gly Phe Leu
    610                 615                 620

Tyr Lys Val Glu Thr Leu His Asp Phe Glu Ala Ala Asn Ser Asp Glu
625                 630                 635                 640

Leu Thr Leu Gln Arg Gly Asp Val Val Leu Val Val Pro Ser Asp Ser
                645                 650                 655

Glu Ala Asp Gln Asp Ala Gly Trp Leu Val Gly Val Lys Glu Ser Asp
            660                 665                 670

Trp Leu Gln Tyr Arg Asp Leu Ala Thr Tyr Lys Gly Leu Phe Pro Glu
        675                 680                 685

Asn Phe Thr Arg Arg Leu Asp
        690                 695

<210> SEQ ID NO 2
<211> LENGTH: 695
<212> TYPE: PRT
<213> ORGANISM: Artificial Sequence
<220> FEATURE:
<223> OTHER INFORMATION: AMPH1 V392G mutant amino acid sequence

<400> SEQUENCE: 2

Met Ala Asp Ile Lys Thr Gly Ile Phe Ala Lys Asn Val Gln Lys Arg
1               5                   10                  15

Leu Asn Arg Ala Gln Glu Lys Val Leu Gln Lys Leu Gly Lys Ala Asp
                20                  25                  30

Glu Thr Lys Asp Glu Gln Phe Glu Glu Tyr Val Gln Asn Phe Lys Arg
            35                  40                  45

Gln Glu Ala Glu Gly Thr Arg Leu Gln Arg Glu Leu Arg Gly Tyr Leu
        50                  55                  60

Ala Ala Ile Lys Gly Met Gln Glu Ala Ser Met Lys Leu Thr Glu Ser
65                  70                  75                  80

Leu His Glu Val Tyr Glu Pro Asp Trp Tyr Gly Arg Glu Asp Val Lys
                85                  90                  95

Met Val Gly Glu Lys Cys Asp Val Leu Trp Asp Phe His Gln Lys
            100                 105                 110

Leu Val Asp Gly Ser Leu Leu Thr Leu Asp Thr Tyr Leu Gly Gln Phe
        115                 120                 125

Pro Asp Ile Lys Asn Arg Ile Ala Lys Arg Ser Arg Lys Leu Val Asp
    130                 135                 140
```

-continued

Tyr Asp Ser Ala Arg His His Leu Glu Ala Leu Gln Ser Ser Lys Arg
145                 150                 155                 160

Lys Asp Glu Ser Arg Ile Ser Lys Ala Glu Glu Phe Gln Lys Ala
            165                 170                 175

Gln Lys Val Phe Glu Phe Asn Val Asp Leu Gln Glu Leu Pro
        180                 185                 190

Ser Leu Trp Ser Arg Arg Val Gly Phe Tyr Val Asn Thr Phe Lys Asn
    195                 200                 205

Val Ser Ser Leu Glu Ala Lys Phe His Lys Glu Ile Ala Val Leu Cys
    210                 215                 220

His Lys Leu Tyr Glu Val Met Thr Lys Leu Gly Asp Gln His Ala Asp
225                 230                 235                 240

Lys Ala Phe Thr Ile Gln Gly Ala Pro Ser Asp Ser Gly Pro Leu Arg
                245                 250                 255

Ile Ala Lys Thr Pro Ser Pro Pro Glu Glu Pro Ser Pro Leu Pro Ser
            260                 265                 270

Pro Thr Ala Ser Pro Asn His Thr Leu Ala Pro Ala Ser Pro Ala Pro
        275                 280                 285

Ala Arg Pro Arg Ser Pro Ser Gln Thr Arg Lys Gly Pro Pro Val Pro
    290                 295                 300

Pro Leu Pro Lys Val Thr Pro Thr Lys Glu Leu Gln Gln Glu Asn Ile
305                 310                 315                 320

Ile Ser Phe Phe Glu Asp Asn Phe Val Pro Glu Ile Ser Val Thr Thr
                325                 330                 335

Pro Ser Gln Asn Glu Val Pro Glu Val Lys Lys Glu Thr Leu Leu
            340                 345                 350

Asp Leu Asp Phe Asp Pro Phe Lys Pro Glu Val Thr Pro Ala Gly Ser
        355                 360                 365

Ala Gly Val Thr His Ser Pro Met Ser Gln Thr Leu Pro Trp Asp Leu
    370                 375                 380

Trp Thr Thr Ser Thr Asp Leu Gly Gln Pro Ala Ser Gly Gly Ser Phe
385                 390                 395                 400

Asn Gly Phe Thr Gln Pro Gln Asp Thr Ser Leu Phe Thr Met Gln Thr
                405                 410                 415

Asp Gln Ser Met Ile Cys Asn Leu Ala Glu Ser Glu Gln Ala Pro Pro
            420                 425                 430

Thr Glu Pro Lys Ala Glu Pro Leu Ala Ala Val Thr Pro Ala Val
        435                 440                 445

Gly Leu Asp Leu Gly Met Asp Thr Arg Ala Glu Glu Pro Val Glu Glu
    450                 455                 460

Ala Val Ile Ile Pro Gly Ala Asp Ala Asp Ala Val Gly Thr Leu
465                 470                 475                 480

Val Ser Ala Ala Glu Gly Ala Pro Gly Glu Glu Ala Glu Ala Glu Lys
                485                 490                 495

Ala Thr Val Pro Ala Gly Glu Gly Val Ser Leu Glu Glu Ala Lys Ile
            500                 505                 510

Gly Thr Glu Thr Glu Gly Ala Glu Ser Ala Gln Pro Glu Ala Glu
        515                 520                 525

Glu Leu Glu Ala Thr Val Pro Gln Lys Val Ile Pro Ser Val Val
    530                 535                 540

Ile Glu Pro Ala Ser Asn His Glu Glu Glu Gly Glu Asn Glu Ile Thr
545                 550                 555                 560

```
Ile Gly Ala Glu Pro Lys Glu Thr Thr Glu Asp Ala Ala Pro Pro Gly
                565             570             575

Pro Thr Ser Glu Thr Pro Glu Leu Ala Thr Glu Gln Lys Pro Ile Gln
            580             585             590

Asp Pro Gln Pro Thr Pro Ser Ala Pro Ala Met Gly Ala Ala Asp Gln
            595             600             605

Leu Ala Ser Ala Arg Glu Ala Ser Gln Glu Leu Pro Pro Gly Phe Leu
            610             615             620

Tyr Lys Val Glu Thr Leu His Asp Phe Glu Ala Ala Asn Ser Asp Glu
625             630             635             640

Leu Thr Leu Gln Arg Gly Asp Val Val Leu Val Val Pro Ser Asp Ser
            645             650             655

Glu Ala Asp Gln Asp Ala Gly Trp Leu Val Gly Val Lys Glu Ser Asp
            660             665             670

Trp Leu Gln Tyr Arg Asp Leu Ala Thr Tyr Lys Gly Leu Phe Pro Glu
            675             680             685

Asn Phe Thr Arg Arg Leu Asp
690             695
```